United States Patent [19]

Young et al.

[11] Patent Number: 5,272,085
[45] Date of Patent: Dec. 21, 1993

[54] SODIUM TOLERANCE GENES DERIVED FROM SCHIZOSACCHAROMYCES POMBE

[75] Inventors: Paul G. Young; Zheng P. Jia, both of Kingston, Canada

[73] Assignee: Queen's University, Kingston, Canada

[21] Appl. No.: 429,538

[22] Filed: Oct. 31, 1989

[51] Int. Cl.⁵ .................. C12N 15/31; C12N 1/19
[52] U.S. Cl. ..................... 435/254.2; 536/23.74; 435/320.1; 435/172.3
[58] Field of Search .............. 435/69.1, 172.3, 255; 536/27; 935/60, 69

[56] References Cited

PUBLICATIONS

Tilbury, R. H., Biotechnology Abstracts (File 357, Dialog), Accession No.; 84–00863, 1983.

*Primary Examiner*—Richard A. Schwartz
*Assistant Examiner*—John L. LeGuyader
*Attorney, Agent, or Firm*—Richard J. Hicks

[57] ABSTRACT

A gene, sod2, which is capable of conferring sodium and lithium tolerance in *Schizosaccharomyces pombe* has been identified and characterized. A plasmid, psod2, consisting of about 5.8 kb of *S. pombe* wild type genomic DNA inserted in a plasmid vector pFL20 has been isolated and used to transfer sodium and lithium tolerance to wild type *S. pombe*. A mutant strain of *S. pombe*, sod2-1, having sodium and lithium tolerance has been selected and shown to have an amplified locus. The amplified locus corresponds to the genomic insert of psod2. The gene or homologues thereof may be inserted into higher life forms, such as plants.

2 Claims, 25 Drawing Sheets

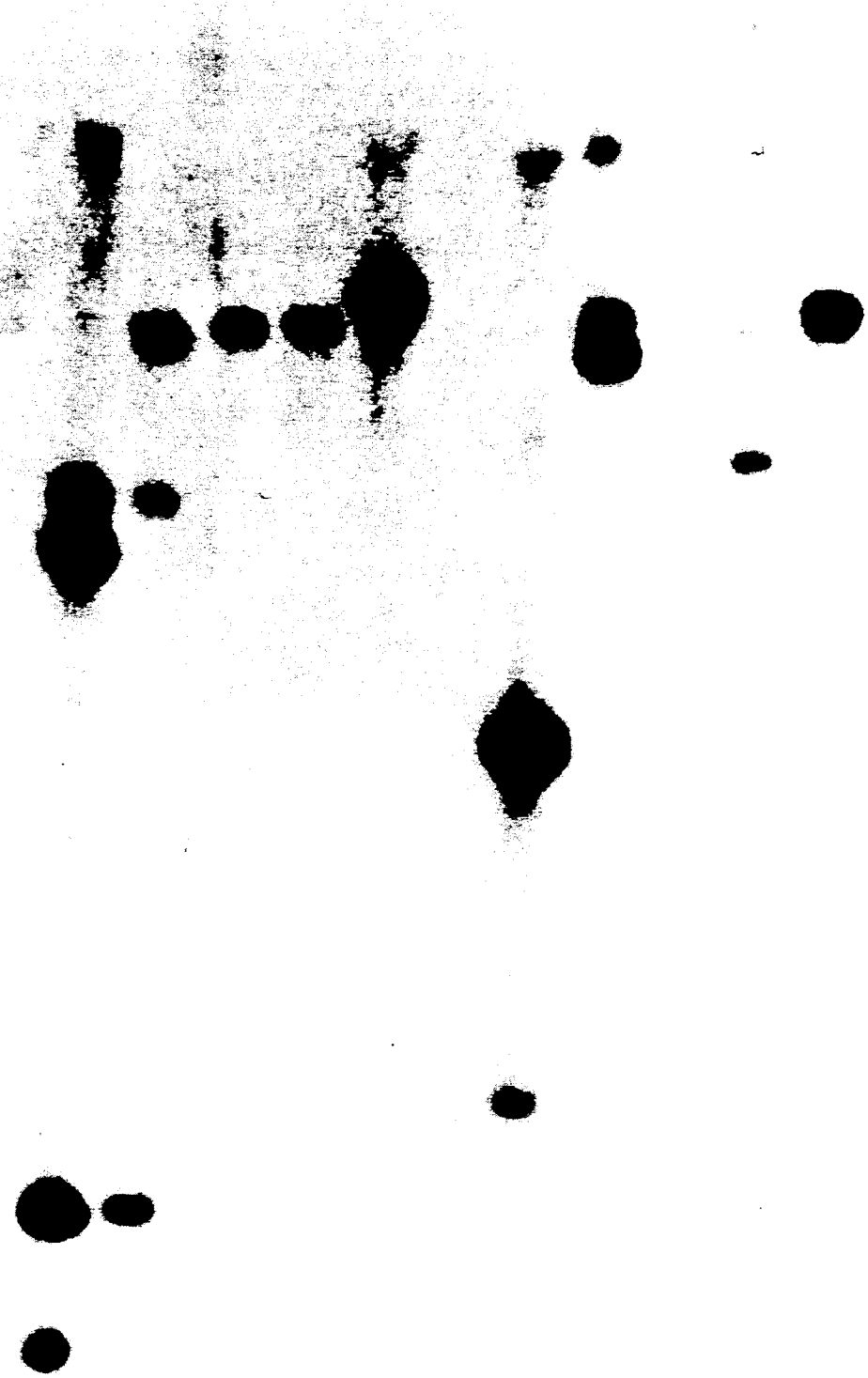
FIG II

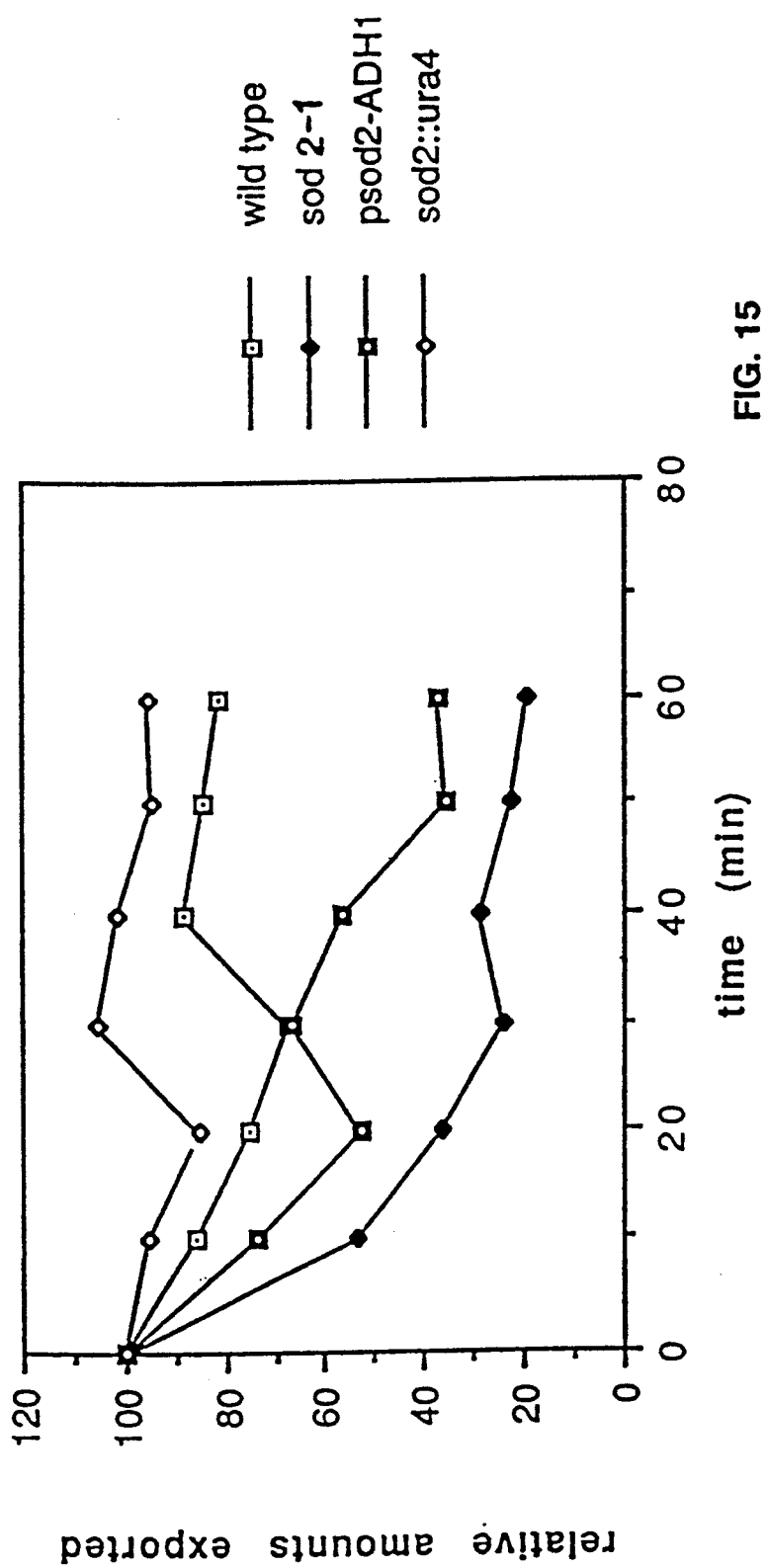

```
             HindIII                         KpnI
  1   aagctttgttactccaatcaaaaagataactaaggtaccccggtcctcaagtataaacca
 61   caggcatgcacgcatcagtccgtggctaactgtatcttttgccacatttttatgtcgaata
121   ctctaaaaaaaatattataggaatttattacaagaaaacattctcttgtggatattgcct 181   aattactATGGGCTGGAGACAACTTGATATAGACAAAGTCCATTTAGCTTTAATAGTGGC
              MetGlyTrpArgGlnLeuAspIleAspLysValHisLeuAlaLeuIleValAla 241   CGGGGGATTTATAACATTTTTCTGCTATTTTTCAGAAGTTTTTCGAAAAAAATTACTAGT
      GlyGlyPheIleThrPhePheCysTyrPheSerGluValPheArgLysLysLeuLeuVal 301   TGGAGAAGCTGgtacgttgaagatattgtatagggtggttttgaaaattagcaattgat
      GlyGluAla 361   ataaaataagactaatactagtgtgtagTTCTTGGAAGTATCACTGGATTAATATTTGGG
                                 ValLeuGlySerIleThrGlyLeuIlePheGly
                                                              NcoI
421   CCTCATGCTGCTAAACTCGTAGACCCTTTTTCCTGGGGTGACCATGGAGATTACTTGACA
      ProHisAlaAlaLysLeuValAspProPheSerTrpGlyAspHisGlyAspTyrLeuThr 481   GTAGAGATTTGTAGAATCGTACTTGATGTGCGTGTGTTTGCTTCTGCAATAGAACTCCCC
      ValGluIleCysArgIleValLeuAspValArgValPheAlaSerAlaIleGluLeuPro 541   GGTGCATATTTTCAACATAATTTTCGAAGCATCATTGTAATGCTATTACCAGTTATGGCT
      GlyAlaTyrPheGlnHisAsnPheArgSerIleIleValMetLeuLeuProValMetAla
                            PvuII      NdeI
601   TACGGGTGGTTAGTTACAGCTGGATTTGCATATGCATTGTTTCCACAAATTAACTTTTTA
      TyrGlyTrpLeuValThrAlaGlyPheAlaTyrAlaLeuPheProGlnIleAsnPheLeu 661   GGATCTTTGCTGATCGCAGGATGTATAACTTCTACTGATCCTGTTCTATCAGCATTGATT
      GlySerLeuLeuIleAlaGlyCysIleThrSerThrAspProValLeuSerAlaLeuIle 721   GTAGGAGAAGGTCCATTAGCTAAAAAGACTCCTGAACGGATTCGGTCTTTATTGATCGCT
      ValGlyGluGlyProLeuAlaLysLysThrProGluArgIleArgSerLeuLeuIleAla 781   GAGTCTGGATGTAATGATGGAATGGCGGTTCCTTTTTTCTATTTTGCTATCAAACTTCTT
      GluSerGlyCysAsnAspGlyMetAlaValProPhePheTyrPheAlaIleLysLeuLeu 841   ACTGTTAAGCCATCGAGGAATGCAGGGAGGGATTGGGTGCTGCTTGTTGTGTTGTATGAA
      ThrValLysProSerArgAsnAlaGlyArgAspTrpValLeuLeuValValLeuTyrGlu 901   TGTGCATTTGGTATATTTTTTGGGTGTGTAATAGGGTATCTTTTATCGTTCATTTTAAAG
      CysAlaPheGlyIlePhePheGlyCysValIleGlyTyrLeuLeuSerPheIleLeuLys 961   CACGCTCAGAAATACCGTTTAATTGATGCTATTAGTTATTATTCCCTTCCGCTAGCGATA
      HisAlaGlnLysTyrArgLeuIleAspAlaIleSerTyrTyrSerLeuProLeuAlaIle
```

FIGURE 16A

```
1021 CCTTTATTATGTTCTGGGATAGGAACTATTATTGGAGTTGATGACCTGTTGATGTCCTTT
     ProLeuLeuCysSerGlyIleGlyThrIleIleGlyValAspAspLeuLeuMetSerPhe

1081 TTTGCTGGAATATTATTTAACTGGAATGATTTATTTTCCAAAAATATATCTGCTTGTTCT
     PheAlaGlyIleLeuPheAsnTrpAsnAspLeuPheSerLysAsnIleSerAlaCysSer
                                                        BclI
1141 GTACCTGCTTTTATTGATCAGACTTTTAGTTTACTATTTTTTACCTATTATGGTACAATC
     ValProAlaPheIleAspGlnThrPheSerLeuLeuPhePheThrTyrTyrGlyThrIle

1201 ATTCCCTGGAATAATTTTAATTGGTCTGTTGAAGGCTTGCCTGTTTGGCGTTTAATTGTC
     IleProTrpAsnAsnPheAsnTrpSerValGluGlyLeuProValTrpArgLeuIleVal

1261 TTTAGCATATTGACTCTAGTTTGTCGTCGATTACCGGTTGTATTTTCGGTGAAGCCTTTA
     PheSerIleLeuThrLeuValCysArgArgLeuProValValPheSerValLysProLeu

1321 GTTCCGGACATTAAGACATGGAAAGAAGCCCTTTTCGTTGGACATTTCGGACCAATAGGG
     ValProAspIleLysThrTrpLysGluAlaLeuPheValGlyHisPheGlyProIleGly

1381 GTTTGCGCAGTTTATATGGCATTTCTTGCAAAATTACTGTTGTCCCCGGATGAAATTGAA
     ValCysAlaValTyrMetAlaPheLeuAlaLysLeuLeuLeuSerProAspGluIleGlu

1441 AAGAGTATTTATGAATCAACTACAGTATTTTCAACACTAAATGAAATAATTTGGCCGATC
     LysSerIleTyrGluSerThrThrValPheSerThrLeuAsnGluIleIleTrpProIle

1501 ATTTCGTTTGTTATCTTATCCTCAATCATTGTTCATGGTTTCAGTATCCATGTATTAGTG
     IleSerPheValIleLeuSerSerIleIleValHisGlyPheSerIleHisValLeuVal

1561 ATTTGGGGAAAGTTAAAAAGTCTGTATTTAAATCGAAAAGTCACCAAGTCCGATTCCGAT
     IleTrpGlyLysLeuLysSerLeuTyrLeuAsnArgLysValThrLysSerAspSerAsp

1621 TTGGAGTTACAAGTAATAGGGGTTGATAAGTCACAGGAAGATTACGTTtaggaaagctct
     LeuGluLeuGlnValIleGlyValAspLysSerGlnGluAspTyrVal 1681 tttaatgtcaattcggatttccaaattattttcaaatgtattgtgaatcgctgtctctgg
1741 tcaaaaagattactgcactcatatttgaaattccttctatagttgatatatactataag
1801 ataagtgattctcagaatcacaaggctaaccaccaacagggatggagtgtatattttgt
1861 tgtacatatatattatctacaatagagtaattttcggcttctataattcatttattttct
                                                        BclI
1921 tactactctaaaaatattgtataatttctaaaactgatcaagatactgagaaaagtacaa
1981 atcgttatttaatttgtaatttattttgatggctaaaacttaccaatattcgttcgcttc
2041 aaacaataccaatcttacgaaacaccttacgcttcatcaaagtctactttggatcaccta
2101 atatttattatttgttgttgtaattatacaaactaatactatttatgtaagaaactaa
2161 gaaaacggaaaatcaatagctactttgtgtatataaatagcaatcaaattaaaacttgat
2241 aaatctcacctactaaaacacatcaacgtacttcaaagggcctaactactataagacttg
                                                        HindIII
2301 gtaatatttaaatagtgtttctattagtaggtagcttcaaagtatgtataa...aagctt
```

FIGURE 16B

SODIUM TOLERANCE GENES DERIVED FROM SCHIZOSACCHAROMYCES POMBE

FIELD OF INVENTION

This invention relates to sodium tolerant strains of *Schizosaccharomyces pombe* and more particularly to the identification and isolation of the genetic locus, sod2, and plasmid psod2 responsible for conferring sodium and lithium tolerance upon wild type *S. pombe*.

BACKGROUND OF INVENTION

The responses of plants and other life forms, such as yeasts, to salt (sodium chloride) and other environmental stresses have been studied extensively for many years. Certain plants and yeasts have been identified as being more "salt tolerant" than others and it has long been hypothesized that such plants and/or yeasts must contain within their genomes at least one gene which is capable of transporting sodium into or out of the cellular structure of the organism. However, after years of study, no such single gene or gene product directly involved in $Na^+$ or $Cl^-$ metabolism has heretofore been identified (Mechanisms of Salinity Tolerance in Plants, T.J. Cheeseman Plant Physiol (1988) 87, 544-550).

Identification and characterization of any such gene or gene product which confers salt tolerance is, of course, of immense commercial potential, regardless of the species in which it is identified. Modern genetic engineering techniques may be employed to transfer the gene to any desired species in which it will be reliably expressed thus raising the possibility of cultivating crops in arid or semi arid areas using saline waters for irrigation purposes, or for producing crops in areas of increasing salinity, such as the coastal plains of California. If a salt tolerant gene is inserted into a yeast, such as brewers yeast, it should be possible to produce ethanol with water or feedstocks having significant salinity—a condition which pertains in many areas of the world.

OBJECTS OF INVENTION

It is an object of the present invention to provide and characterize a gene (sod2) which confers salt tolerance in yeasts and plants.

It is another object of the present invention to isolate and characterize a plasmid (psod2) consisting of a portion of the *Schizosaccharomyces pombe* wild type genome. This plasmid has the property of conferring sodium and lithium resistance upon wild type *S. pombe*.

It is yet another object of the present invention to provide mutant strains of *S. pombe* which overexpress the sod2 gene and thereby conder sodium and lithium tolerance.

BRIEF STATEMENT OF INVENTION

By one aspect of the this invention there is provided a gene capable of conferring sodium and lithium tolerance on wild type *Schizosaccharomyces pombe*;

By another aspect of this invention there is provided a plasmid, psod2, consisting of a 5.8 kb *S. pombe* wild type genomic DNA insert in plasmid vector pFL20, which is capable of conferring sodium and lithium resistance upon wild type *S. pombe*; and By yet another aspect of this invention there is provided a sodium and lithium tolerant strain of *S. pombe*, sod2-1 ATCC 74028.

BRIEF DESCRIPTION OF DRAWINGS

FIG. 11 is a Southern analysis of genomic DNA from sod2::ura4.

FIG. 15 same as FIG. 14 but with external sodium.

FIG. 16, parts A and B is the nucleotide and amino acid sequence of the sod 2 gene.

DETAILED DESCRIPTION OF PREFERRED EMBODIMENTS

Figure 1A:
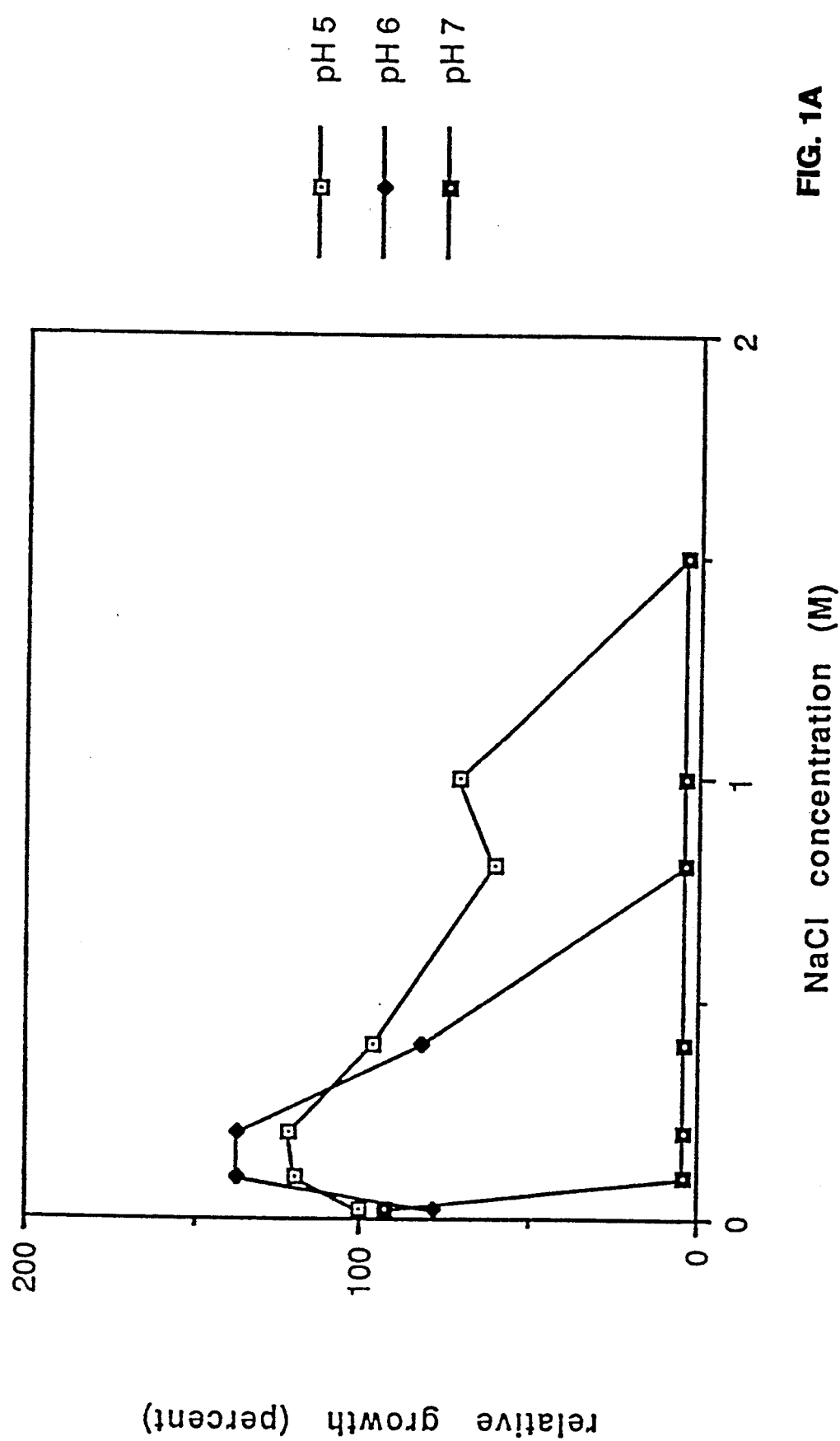
FIGS. 1A, B and C are graphs illustrating pH dependence of cation tolerance.
Figure 1B:
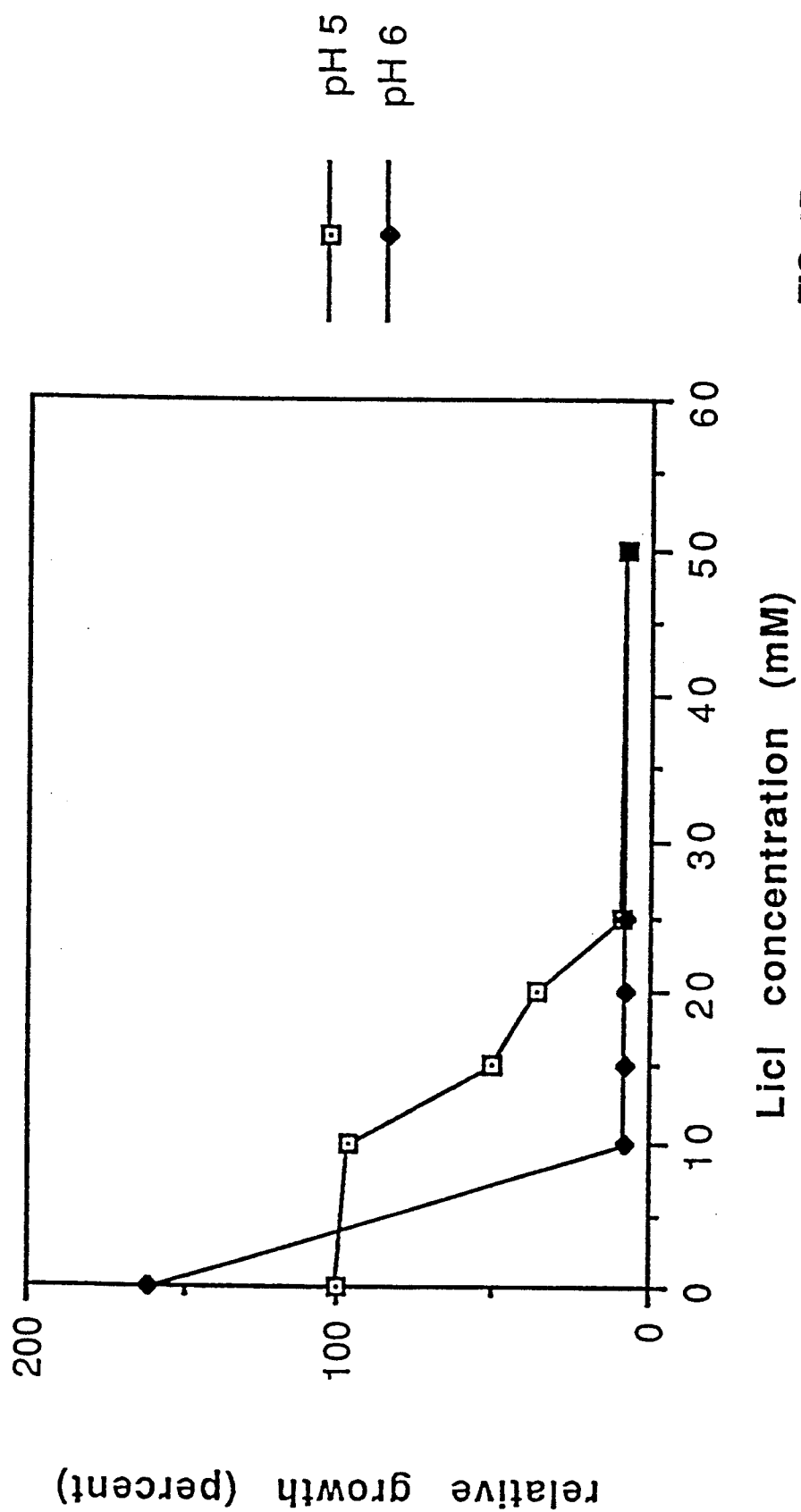
Figure 1C:
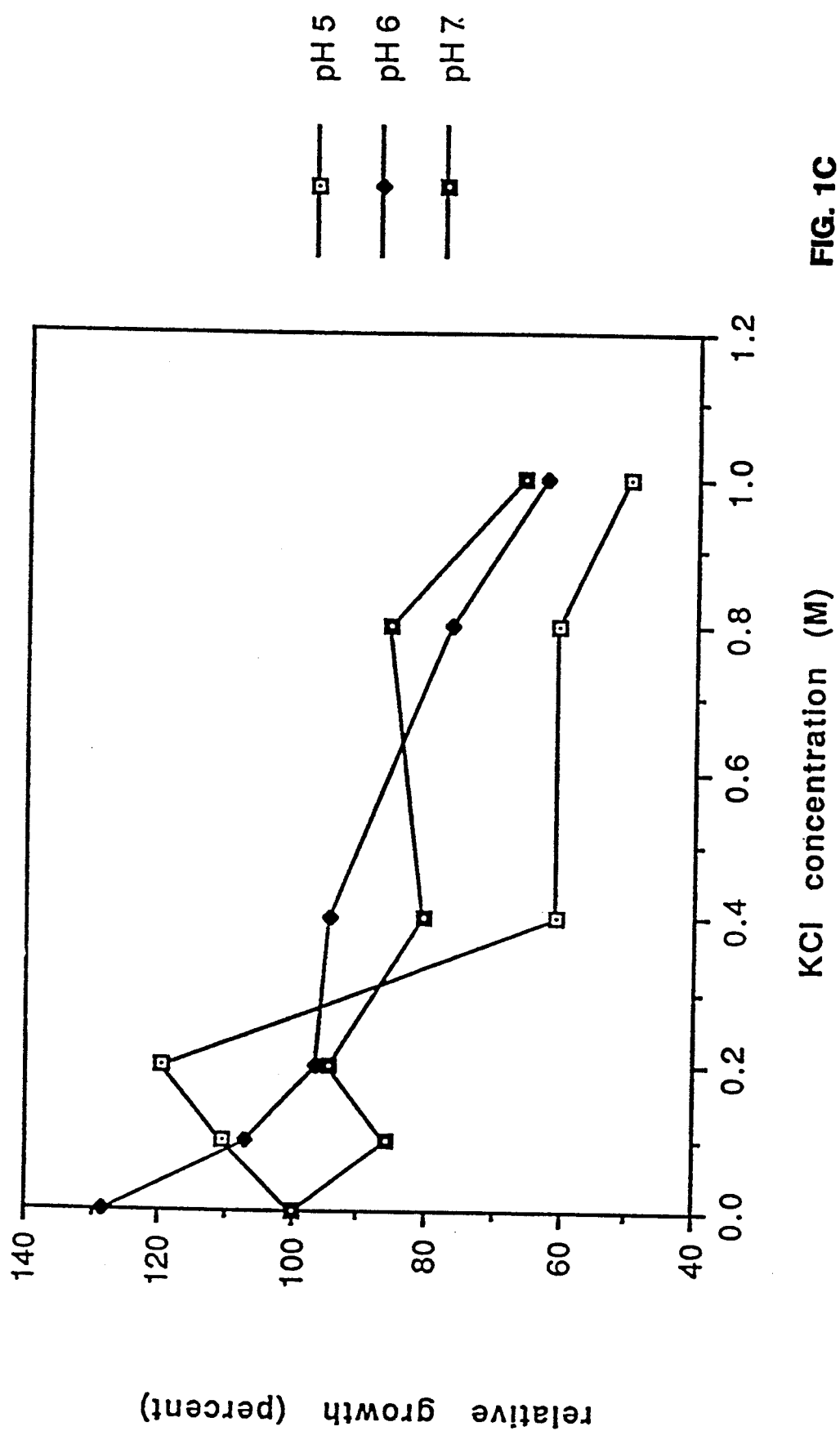

The tolerance of and ability to grow in solutions containing high concentrations of NaCl, KCl or LiCl at various pH levels of wild type (strain 972) *Schizosaccharomyces pombe* was evaluated by plating actively growing cells onto Edinburgh Minimal Medium (EMM) agar plates [EMM. per liter of water: 3 g potassium hydrogen pthalate; 1.8 g disodium hydrogen phosphate (anhydrous); 5 g ammonium chloride; 20 g glucose; 20 ml salt solution (per 2 liter: 107 g $MgCl_2$ 6 $H_2O$, 2 g $CaCl_2$, 100 g KCl, 4 g $Na_2SO_4$); 1 ml vitamin solution (per 500 ml: 5 g inositol, 5 g nicotinic acid, 0.5 g calcium pantothenate, 5 mg biotin); 0.1 ml trace minerals (per 200 ml: 1 g $H_3BO_3$, 1.04 g $MnSO_4$ $4H_2O$, 0.8 g $ZnSO_4$ 7 $H_2O$, 0.4 g $FeCl_3$ 6 $H_2O$, 0.228 g $KMnO_4$, 80 mg $CuSO_4$ 5 $H_2O$, 2 g citric acid, 20 mg KI) [Mitchison (1970), Nurse (1975)] supplemented with various concentrations of the appropriate test salt. Colony growth and survival were monitored over a period of several days. Relative growth rate was estimated by measuring colony diameter with an ocular micrometer at 48 hr. Multiple colonies for measurement were chosen at random. The experiment was internally controlled for slight differences in growth rate between different plates by plating the tested strains in different regions of the same plate. Typical data are shown in FIG. 1a–c. NaCl and LiCl tolerance were found to be markedly affected by pH, behaving in a parallel fashion but with LiCl being considerably more toxic than NaCl. At high sodium and lithium concentrations cellular growth rates were impaired or, at the highest levels, cells were killed. KCl tolerance was not affected markedly by pH.

Mutants capable of growing under high NaCl conditions were isolated. A typical genetic screen was as follows. Rapidly growing wild type *Schizosaccharomyces pombe* cells (strain 972), which are freely available from the American Type Culture Collection under accession numbers ATCC 24969, ATCC 26189 and ATCC 38366, were harvested by centrifugation and resuspended in 0.1 molar sodium acetate pH4 containing 0.4 mg/mL nitrosoguanidine for mutagenesis. Cells were allowed to sit in the dark for 30 min. and then washed several times with distilled water by centrifugation. Cells were then plated at densities ranging from $10^6$ to $10^7$ cells per plate on EMM agar plates (pH5.5) supplemented with LiCl at 30 mM. Non-mutagenized wild type cells are killed by these conditions. LiCl was chosen since the wild type growth response to LiCl at various pH level parallels that to NaCl yet LiCl is far more toxic and thus avoids concentration-dependent osmotic effects complicating the screen. After incubation for several days survivors were transferred to EMM plates for further analysis. A total of 20 strains were collected. Most mutant strains were unstable and upon incubation on EMM lost their LiCl tolerance as determined by subsequent retesting. A number of relatively stable strains were detected and further analyzed. These strains were screened for NaCl tolerance and strains growing on EMM plates supplemented with high levels of NaCl were isolated. Following outcrossing and reisolation of sodium and lithium tolerant strains ten such strains were intercrossed and assigned to a single linkage group, designated sod2. Some meiotic instability was noted for all alleles. Typically a sodium resistant strain when outcrossed to wild type would segregate 2:2 strong sodium or lithium resistance to wild type or weak sodium or lithium tolerance. A number of cells displayed intermediate levels of resistance. This is probably explained by unequal crossing-over at an amplified locus.

Strain sod2-1 was crossed to ade6-210 to create a sod2-1 ade6-210 double mutant which was in turn used to complement ade6-216 in a diploid. The diploid created, sod2-1/wild type ade6-210/ade6-216, was LiCl and NaCl resistant demonstrating that the mutation was dominant.

Figure 2:
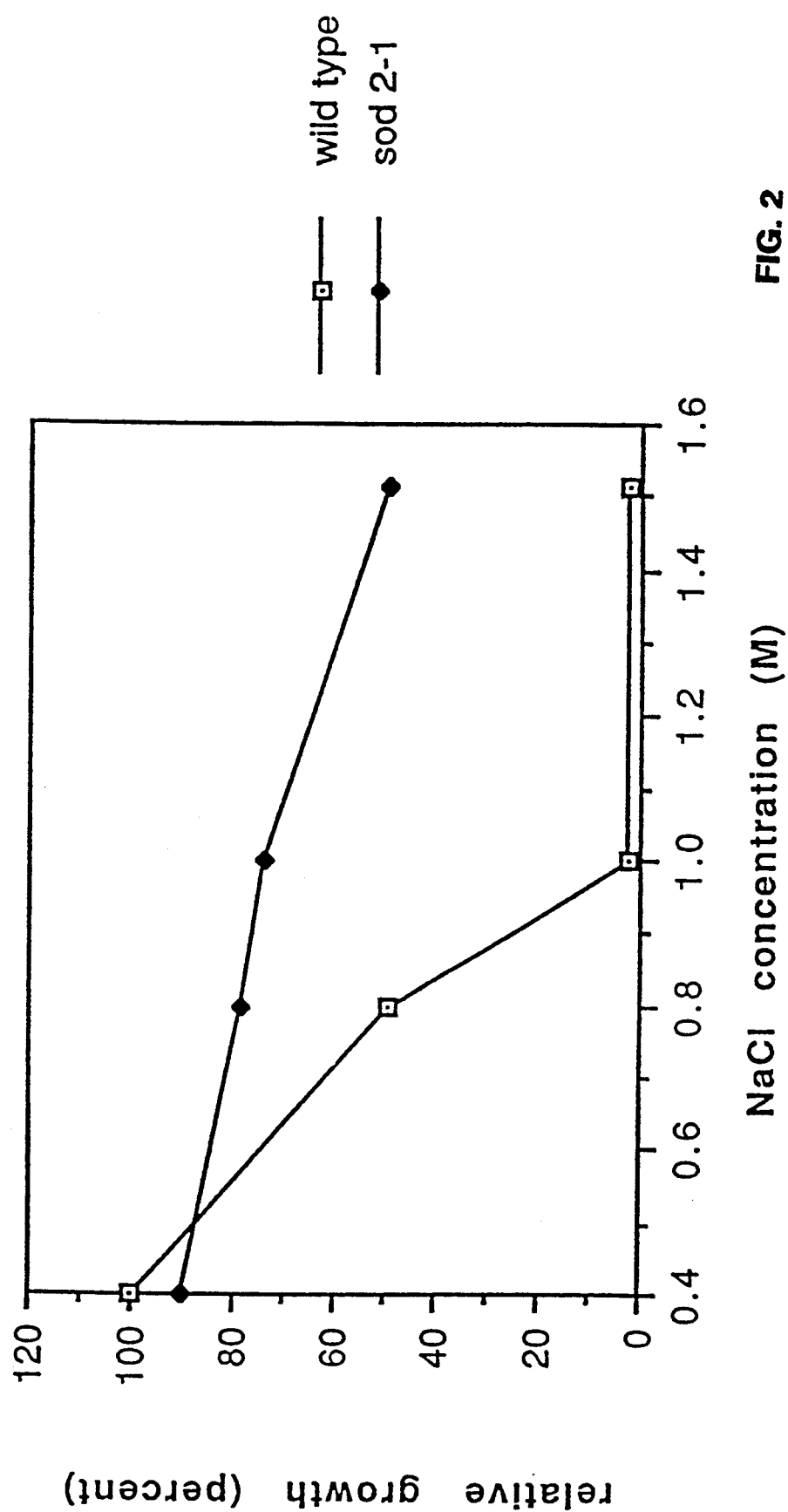
FIG. 2 is a graph illustrating relative growth rate of wild type and sod2-1 *S. pombe* cells on agar plates at high sodium chloride concentrations.
Figure 3A:
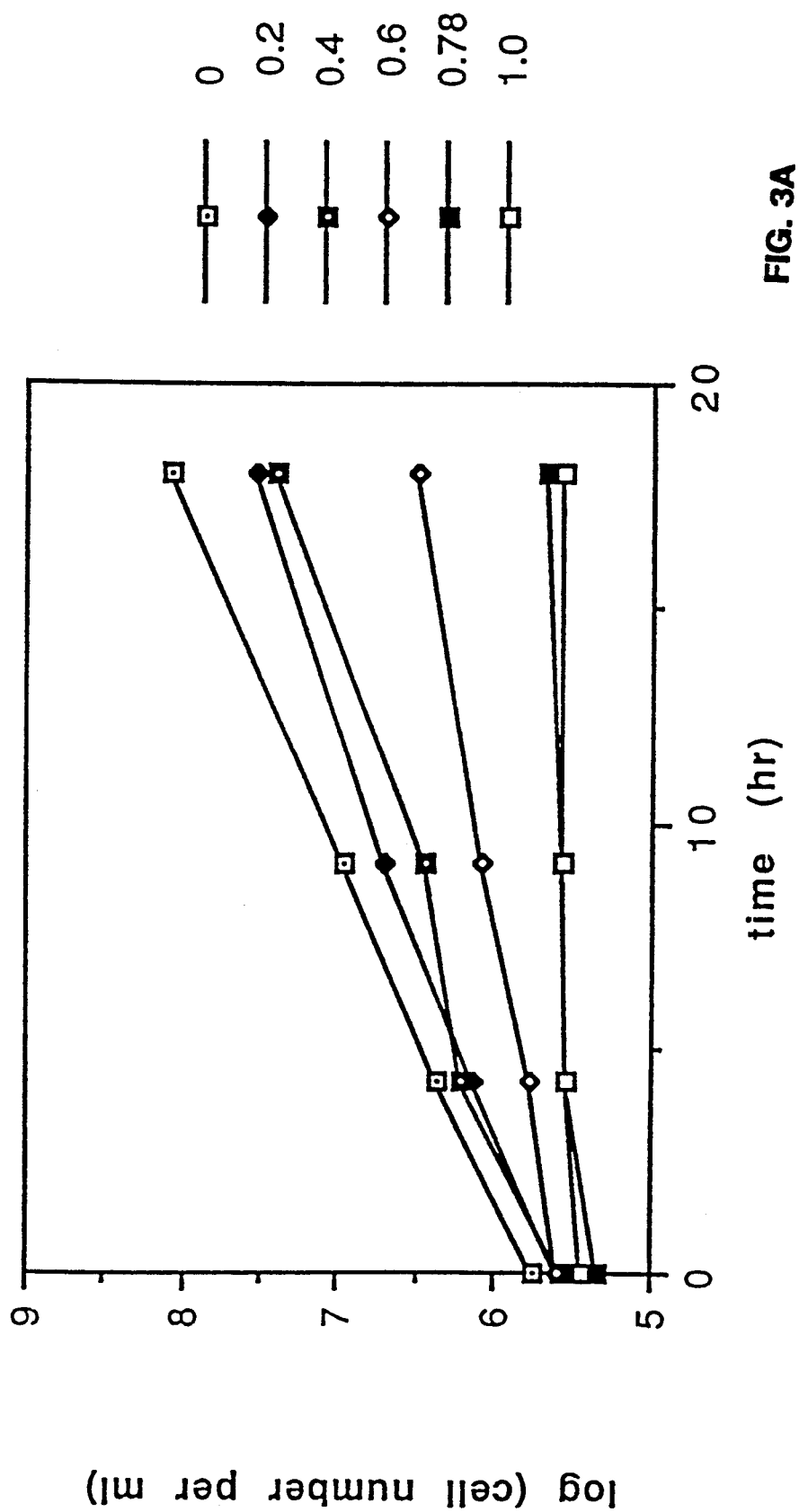
FIGS. 3A, B and C are graphs illustrating growth rate of wild type, sod2-1 and psod2 ura4-d18 *S. pombe* cells in liquid culture relative to NaCl concentration.
Figure 3B:
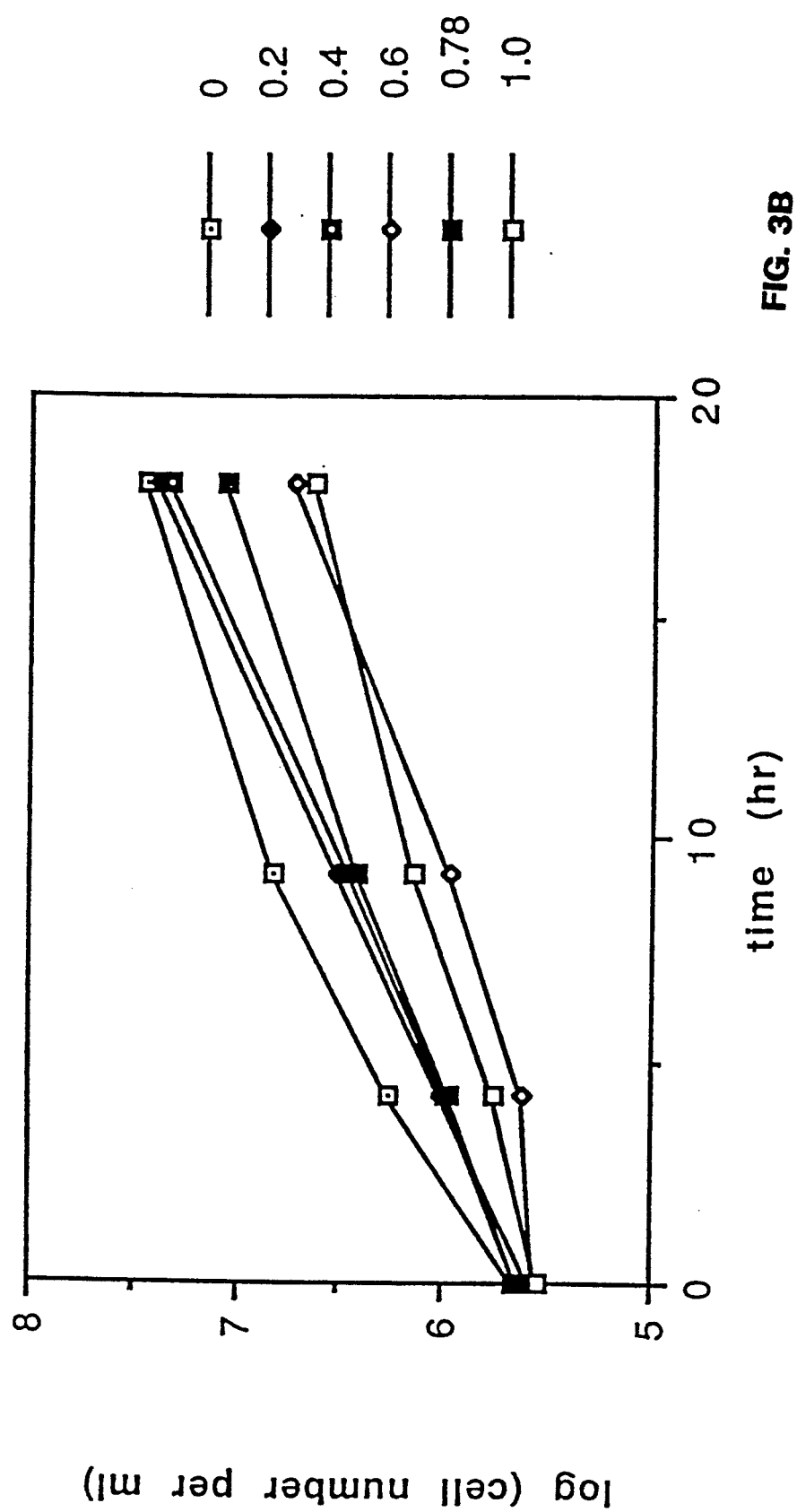
Figure 3C:
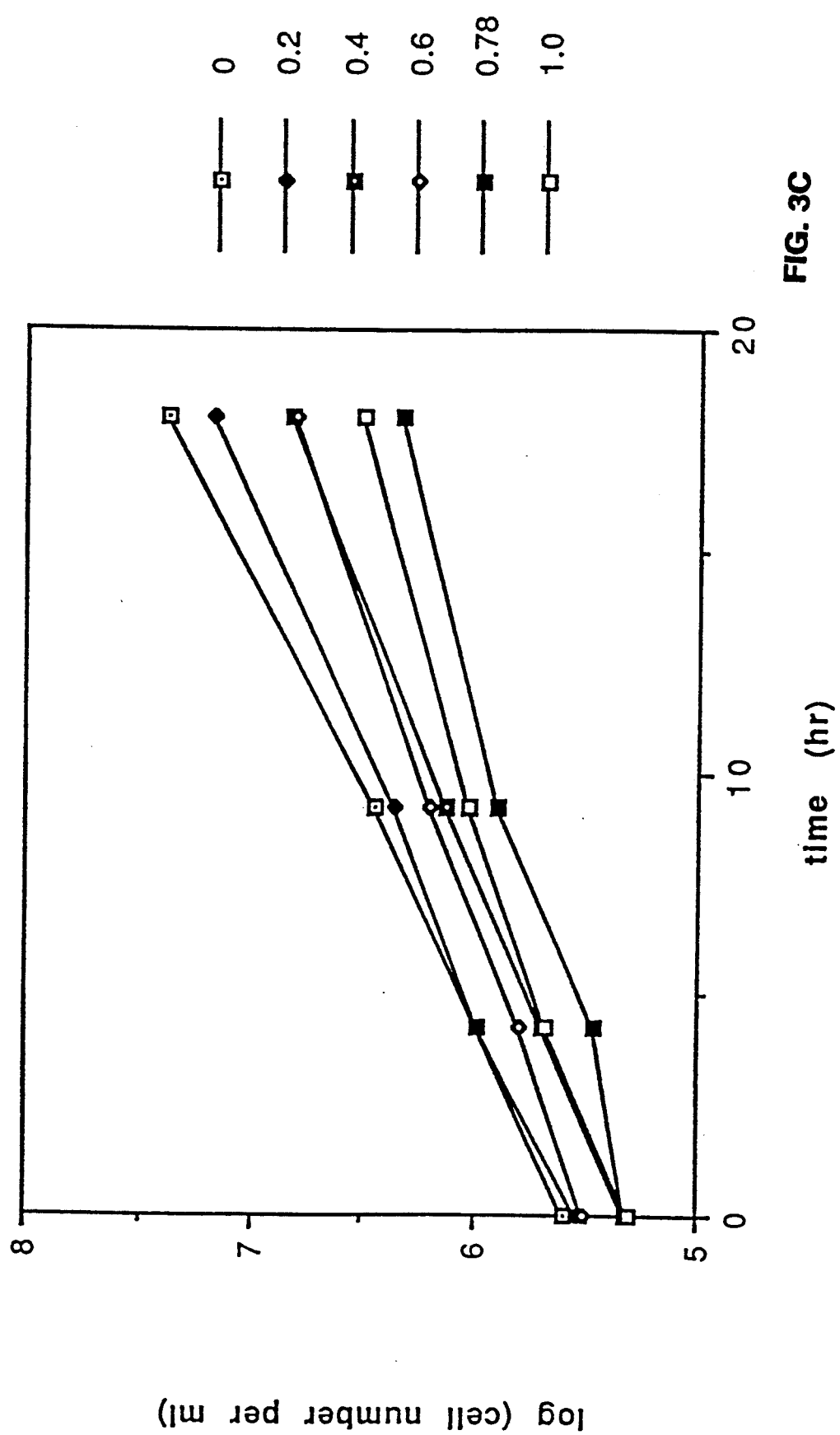
Figure 4A:
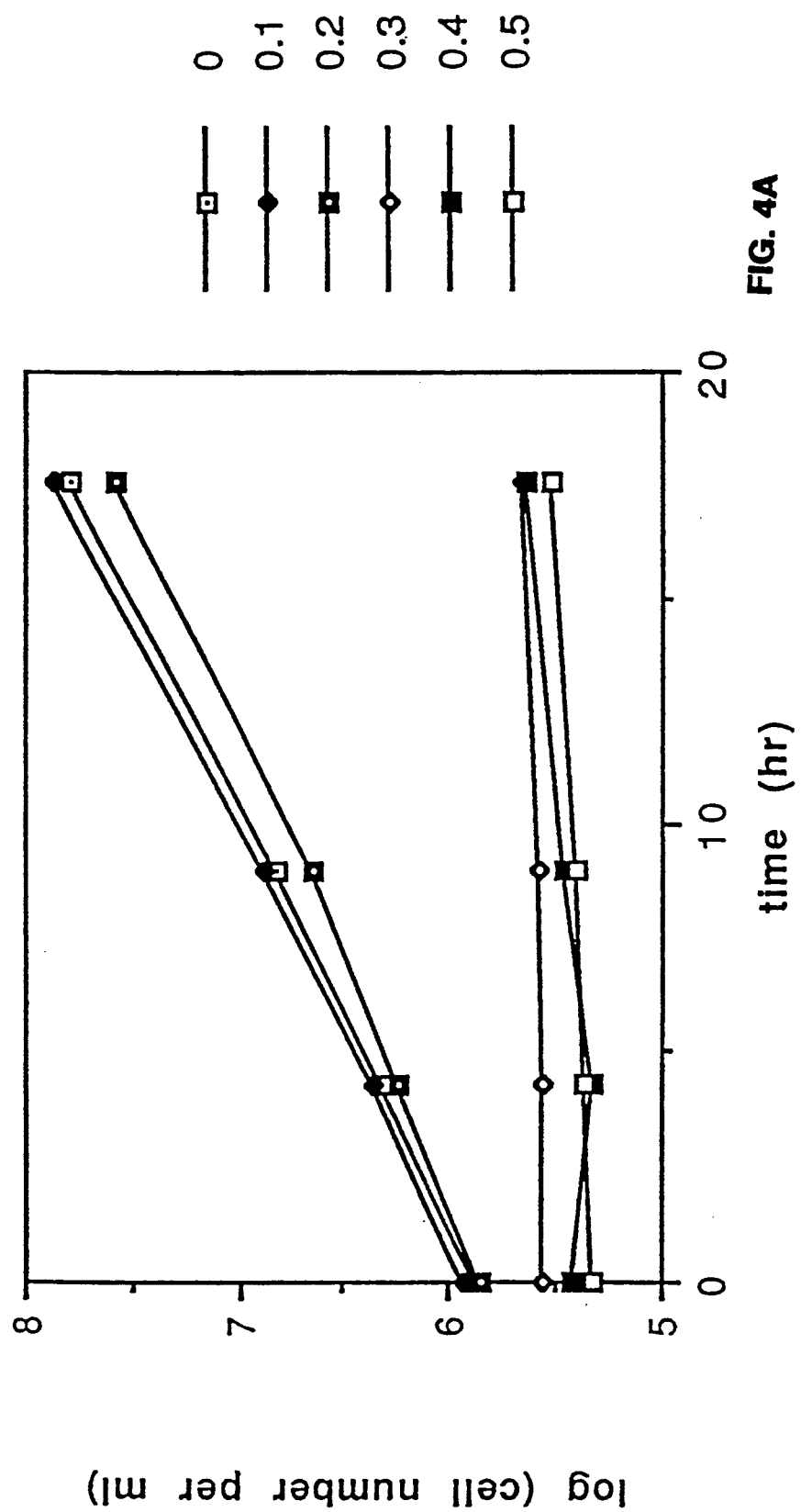
FIGS. 4A, B and C are graphs illustrating growth rate of wild type sod2-1, and psod2 ura4-d18 *S. pombe* cells in liquid culture relative to $Na_2SO_4$ concentration.
Figure 4B:
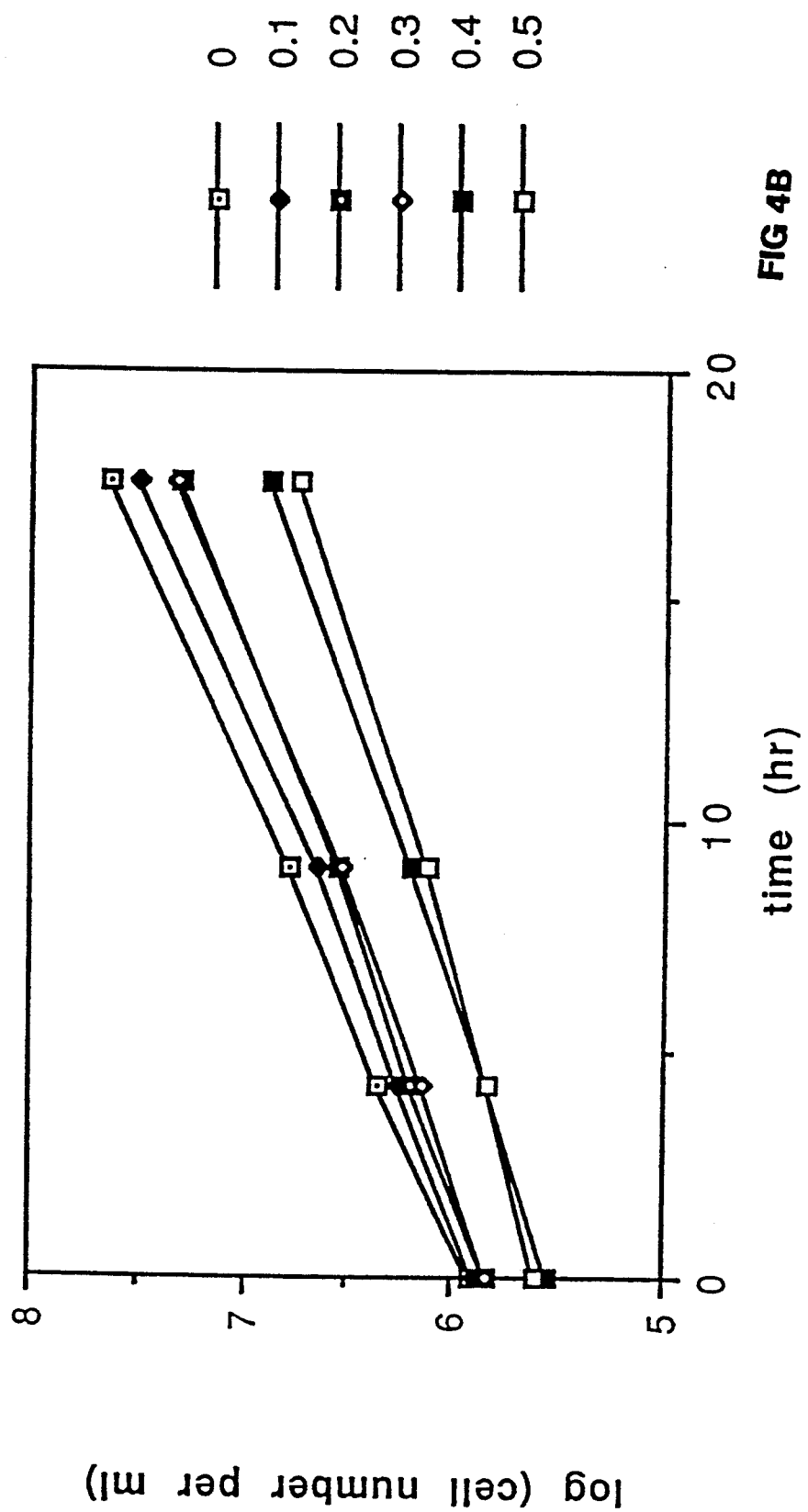
Figure 4C:
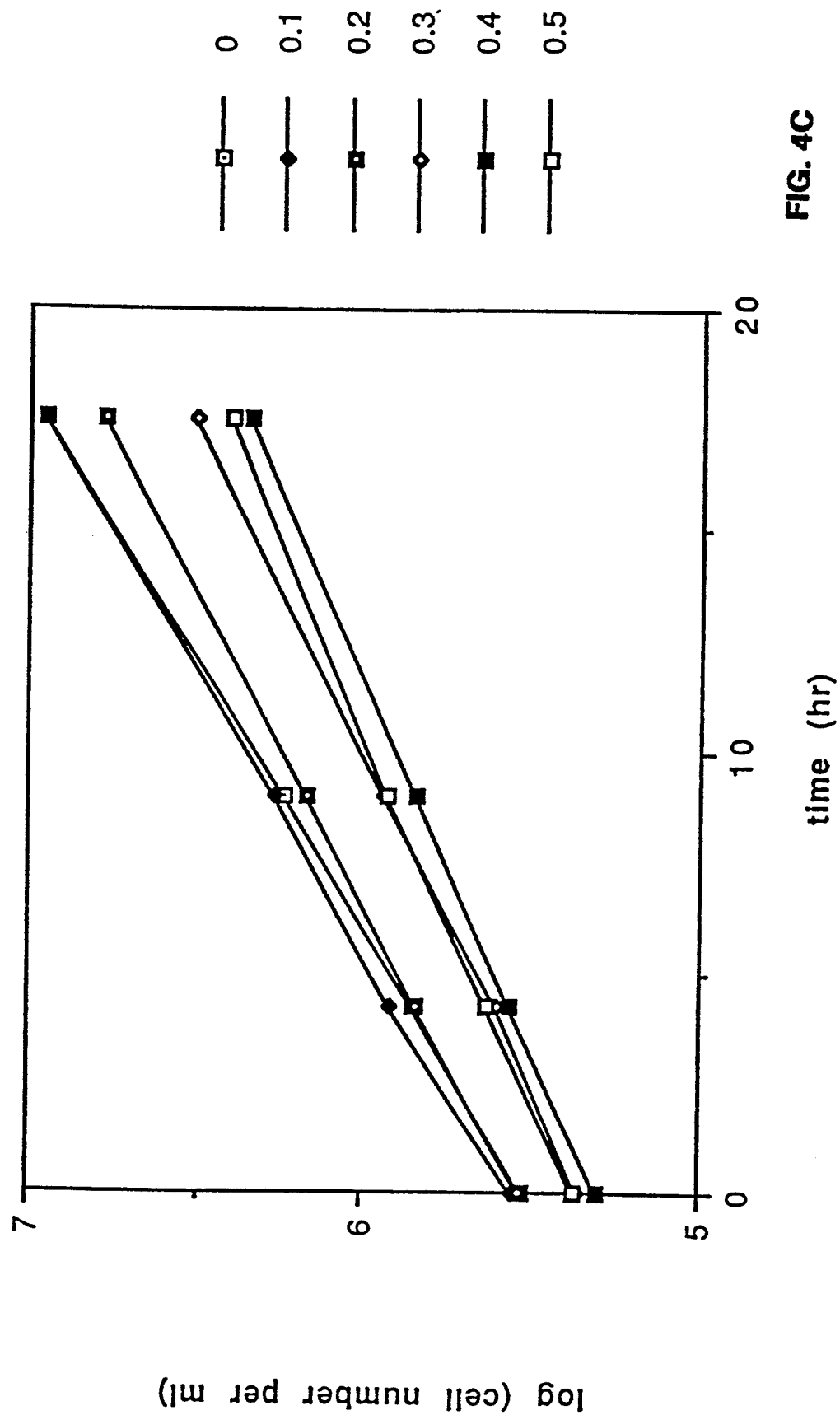

Sod2-1 can grow on higher concentrations of sodium than wild type cells (FIG. 2) This resistance is sodium specific and does not affect potassium tolerance. To confirm the sodium tolerance of the strain in liquid culture, wild type and mutant and plasmid containing (psod2 is a plasmid carrying the sod2 gene, see molecular biology section below) cell lines were incubated in EMM supplemented with various concentrations of NaCl (FIG. 3a–c). Each cell type was grown overnight in EMM, concentrated by centrifugation and then resuspended in a series of flasks in EMM supplemented as indicated. The flasks were then placed in a gyratory shaker at 30° C. and after a 4 hr stabilization period aliquots were removed over time as indicated for cell number determinations in a Coulter Counter. A. wild type; B. sod2-1; C. psod2 ura4-D18. Sod2-1 which has been deposited in the American Type Culture Collection under accession number 74028 was markedly more resistant to NaCl than was wild type. To ensure that a generalized osmotic response was not involved, strains were tested for KCl tolerance. No effect on KCl tolerance was observed. To confirm that acidification of the media did not affect these latter results the pH was monitored after termination of the experiment and found to be typical of EMM (pH 5.1–5.6) in the various cultures. Similar experiments were performed to test for the effect of the cation $Cl^-$ versus $SO_4^=$. No major difference was found (FIG. 4a, b, c).

$^{22}$Na transport studies

Figure 5:
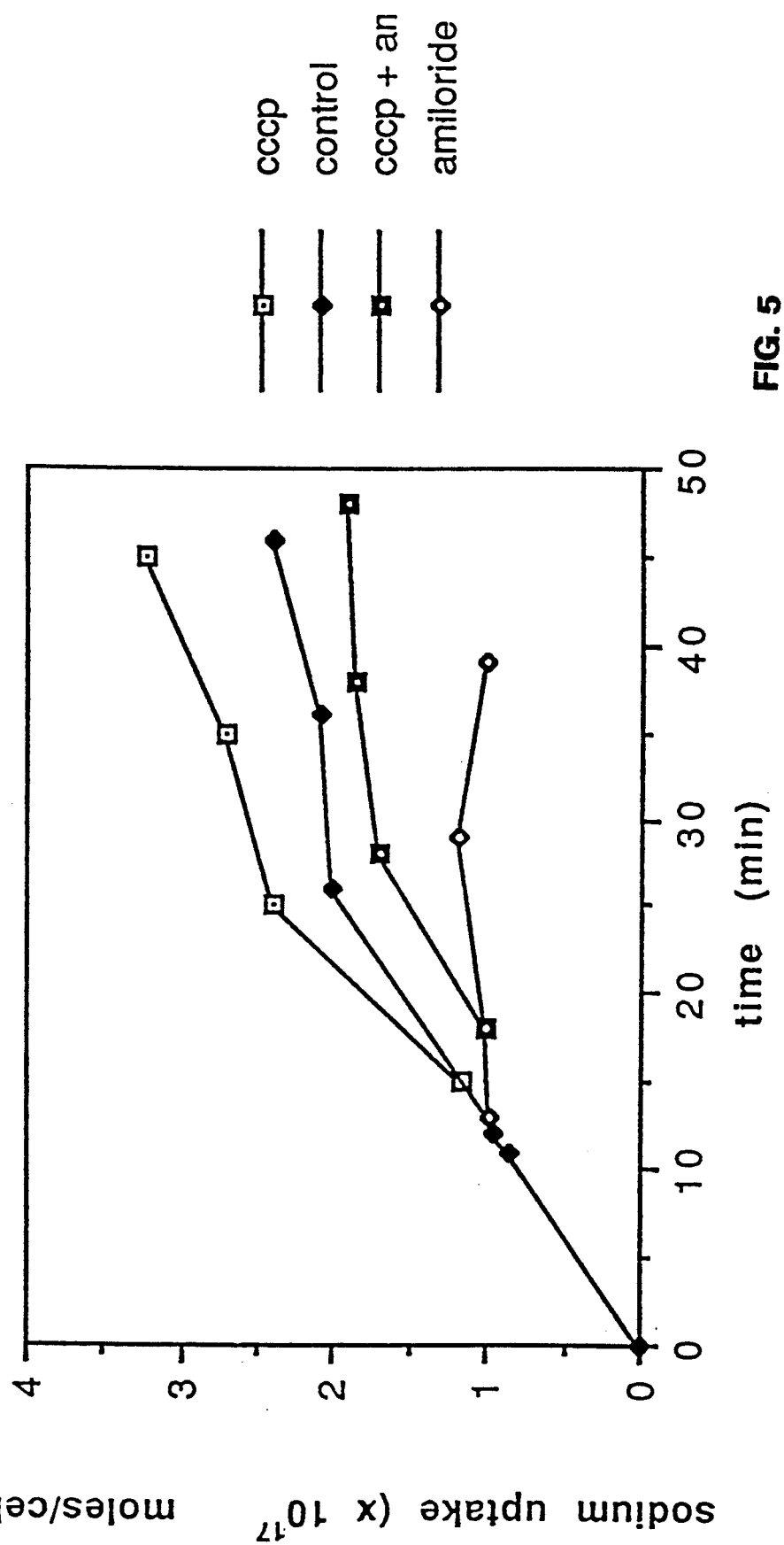
FIG. 5 is a graph illustrating sodium uptake in wild type *S. pombe* cells.
Figure 6:
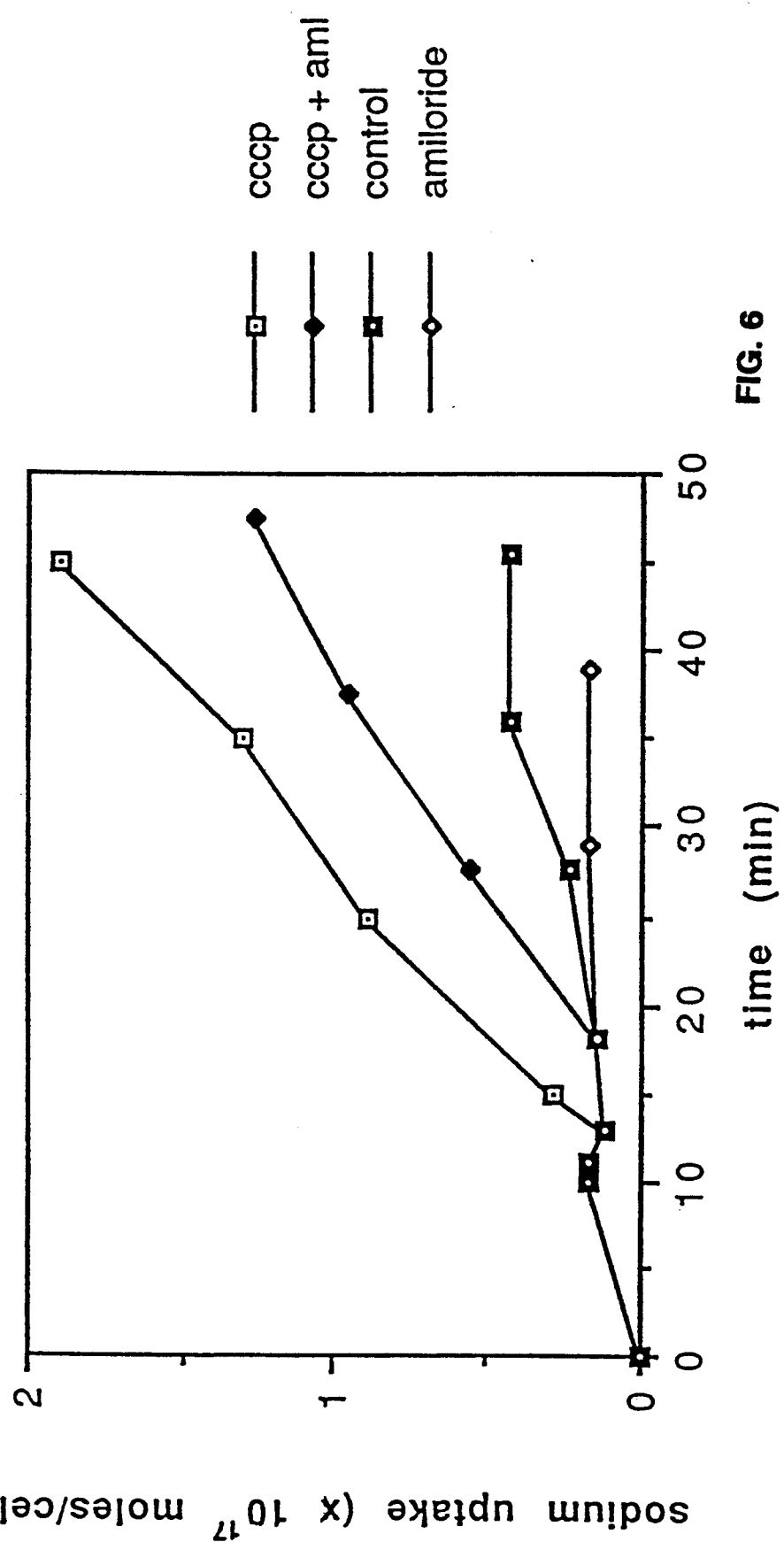
FIG. 6 is a graph illustrating sodium uptake in sod2-1 *S. pombe* cells.

Sodium transport studies in wild type and mutant strains were undertaken. $^{22}$Na uptake and export experiments were performed to compare sod2-1 with wild type cells. For uptake studies cells were washed and resuspended in 5 mM MES (2-(N-morpholino)-ethanesulfonic acid), 5 mM PIPES (piperazine-N,N'-bis(2-ethanesulfonic acid)) buffer at pH 5 and containing 5 mM NaCl and 1 Ci per ml of $^{22}$Na. A kinetic analysis of uptake in wild type cells had previously shown that the uptake rate was saturated at this level of exogenous NaCl. Following incubation, aliquots of the cultures were collected by filtration then washed with a LiCl stop solution and the radioactivity in the cells quantitated in a scintillation counter. At the points indicated the cultures were split and amiloride (100M), CCCP (carboxyl cyanide m-chlorophenyl hydrozone) (6M) or both amiloride and CCCP were added. Sampling then continued in the parallel cultures as indicated. Sodium uptake is expressed as net moles Na per cell. When wild type and sod2-1 were compared under these conditions, sod2-1 cells were found to have a far lower net uptake rate than wild type cells (FIGS. 5 and 6). Since these were net uptake experiments the difference in level between wild type and sod2-1 could have been due either to reduced uptake rates or increased export rates. Whichever the case the experiment provides a simple explanation for the NaCl tolerance.

Figure 7:
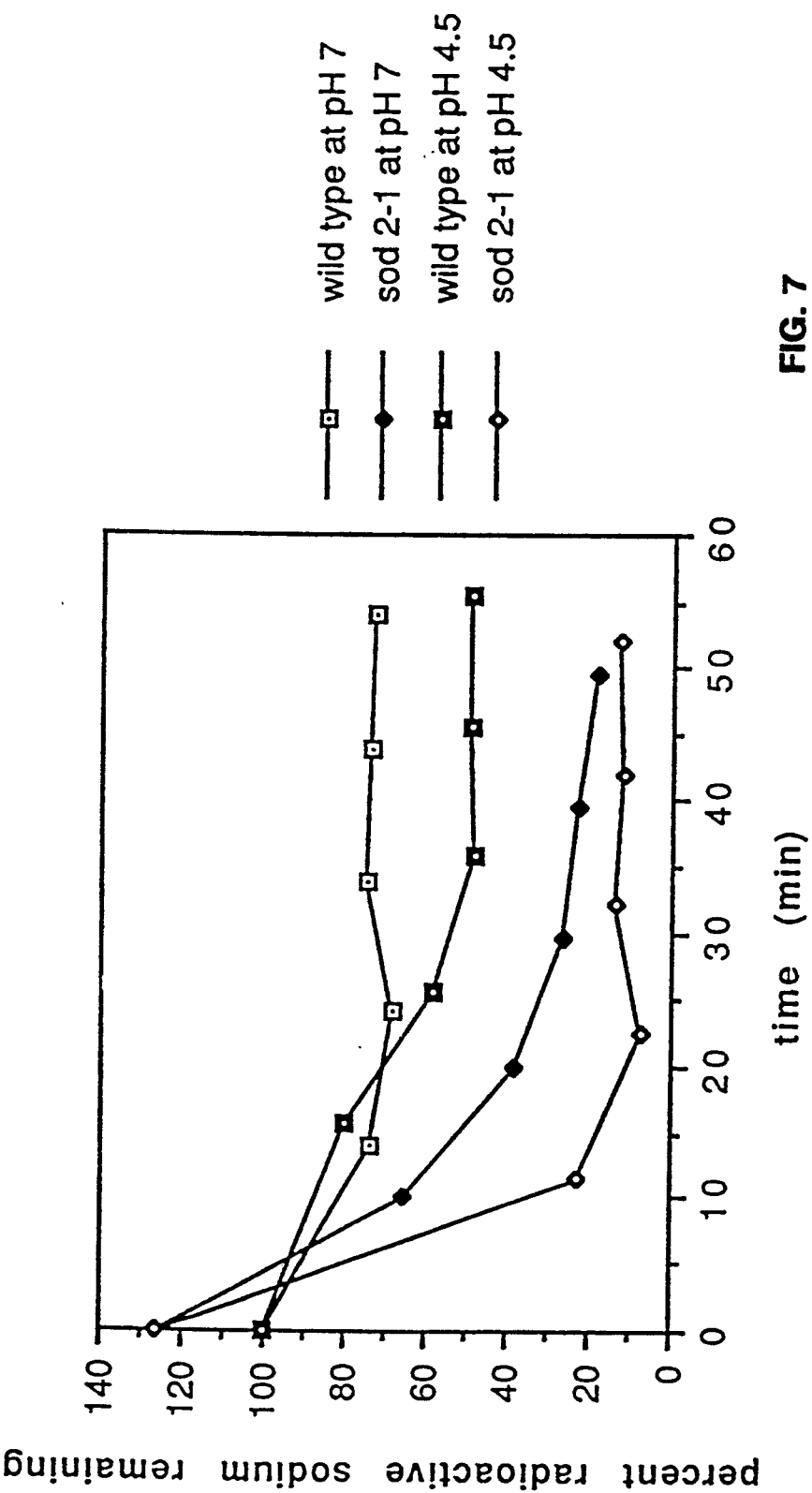
FIG. 7 is a graph illustrating sodium export from wild type and sod2-1 *S. pombe* cells.

Sodium export rates were measured by pre-loading the cells (either wild type or sod2-1) with $^{22}$Na in MES/PIPES as described above at pH 7.0 (conditions under which net sodium uptake rates are high) and then washing the cells by filtration and resuspending them in MES/PIPES plus 5 mM non-radioactive NaCl at pH 7.0 or pH 5.0. The $^{22}$Na content of the cells was then followed by sampling aliquots of the cultures by filtration at timed intervals. sod2-1 exported $^{22}$Na at a higher rate than wild type (FIG. 7).

Molecular characterization

Figure 8:
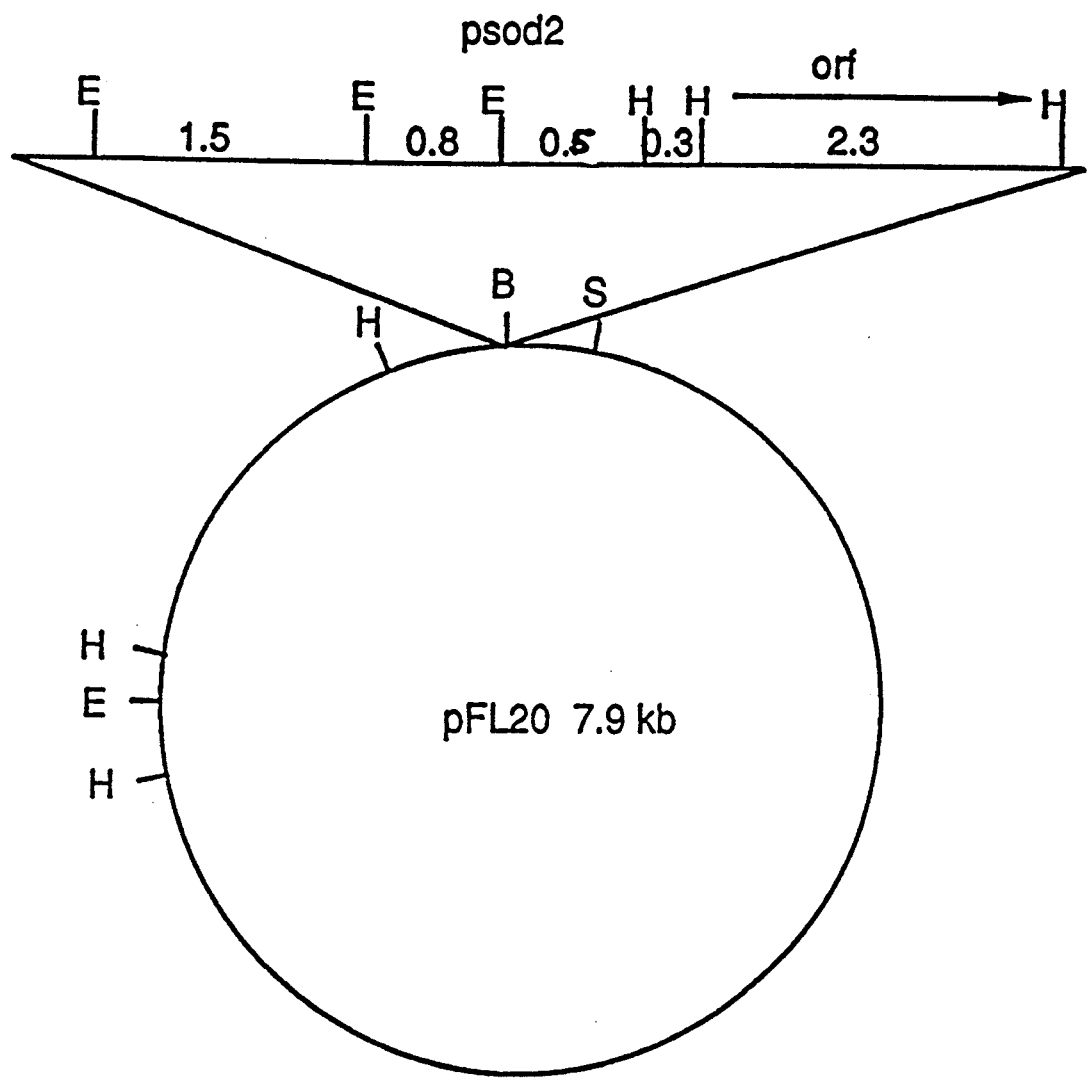
FIG. 8 is a sketch illustrating the plasmid map of psod2.

If the sod2 gene represents an export pump system or regulator of such a system then overexpressing the wild type version of the gene on a multiple copy plasmid should be sufficient to protect a cell from high Na$^+$ or Li$^+$ environments. sod2+ ura4-D18 *S. pombe* were therefore transformed with an *S. pombe* genomic DNA library in plasmid vector pFL20 (Clark and Carbon, 1984). Cells were transformed using NovoZyme 234 (Novo Industri) for cell wall removal and protoplast formation (Beach and Nurse, 1981). Cells were plated on media (EMM with appropriate auxotrophic supplements plus 1.2M sorbitol) lacking uracil. Surviving strains (those carrying a plasmid complementing the uracil auxotrophy) were subsequently replica plated to 30 mM LiCl plates for testing. Two survivor yeast strains were isolated and plasmids prepared as follows. Cells were washed in 20 mM tris(hydroxymethyl)aminomethane, 50 mM ethylenediaminetetraacetic acid, pH 7.4 then resuspended in the same buffer and broken by vortex mixing with an equal volume of 400 micron glass beads. The supernatant was collected, phenol/chloroform extracted and the nucleic acids precipitated with isopropanol. The precipitate was redissolved in 10 mM tris (hydroxymethyl)aminomethane, 2 mM ethylenediaminetetraacetic acid, pH 7.4, digested with ribonuclease A then proteinase K, phenol/chloroform extracted and precipitated with ethanol. The nucleic acid pellet was redissolved as before and transformed into *E. coli* JM109 made competent by $CaCl_2$ washes. The *E. coli* were plated on L-broth containing 40g/mL ampicillin. A bacterial colony from each preparation was then used to prepare plasmids. Two plasmids were obtained, both representing the same sequence as judged by digestion with a variety of restriction endonucleases. The yeast genomic DNA insert was 5.8 kb long. The plasmid was designated psod2 (FIG. 8). The genomic insert is a Sau3A fragment inserted in the pFL20 BamHI site. All units are in kilobases. E=EcoRI; H=HindIII; B=BamHi; S=SphI.

The psod2 plasmid by itself was capable of transforming wild type S. pombe cells to lithium and sodium tolerance (FIG. 3c).

Figure 9:
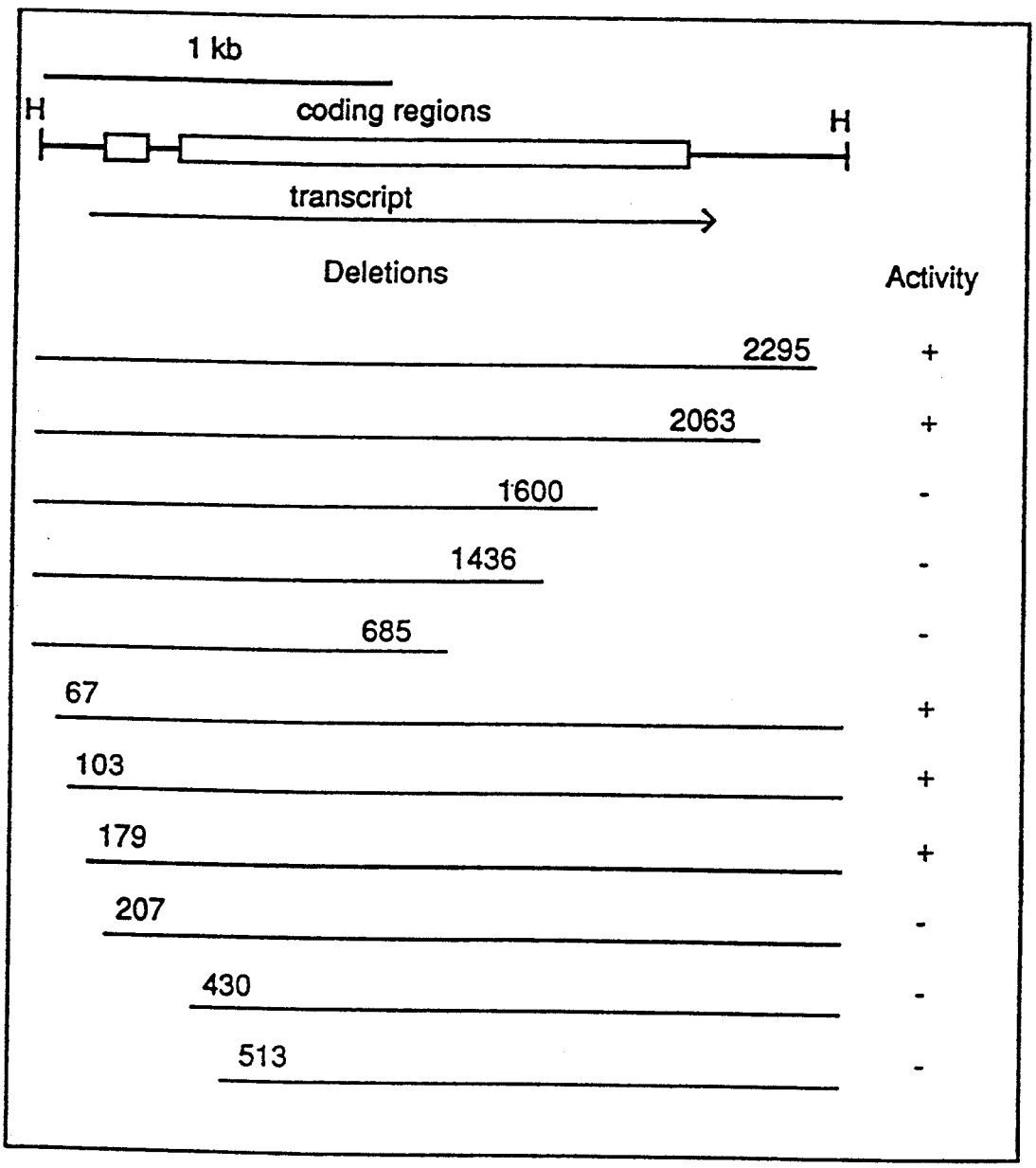
FIG. 9 is a sketch illustrating the coding region and deletion map of the sod2 gene.

Subcloning of a 2.3 kb HindIII fragment from psod2 into pFL20 showed sodium tolerance activity to be located in this portion of the psod2 plasmid. An EcoRI-SalI fragment flanking the 2.3 kb HindIII portion from the 5.8 kb-pFL20 isolate was subcloned into pUC118 and a nested set of deletions made using exonuclease III from the SalI end (Henikoff, 1984 in kit form from Promega). The HindIII 2.3 kb fragment was subcloned into pUC119 and a similar set of deletions made in the opposite orientation. Each construct was tested for sodium/lithium tolerance activity following cotransformation with pWH5 into a sod2+ leu1-32 strain. Cotransformation was necessary since pUC118/119 does not carry a selectable auxotrophic marker for yeast. The results for some of these deletions, defining the upstream and downstream requirement for the active gene are shown in FIG. 9. FIG. 9 also contains an interpretation of the gene structure based on sequence analysis. The structure of the sod2 gene as determined by sequence, $S_1$, primer extension and Northern Blotting analyses as well as functional testing is shown. A positive score indicates survival and growth on the LiCl plate.

Using the same sets of nested deletions in pUC118/119, the gene was sequenced from single stranded templates prepared using M13K07 phage. The sequence was obtained using a dideoxyribonucleotide triphosphate/Sequenase sequencing protocol (Applied Biosystems). Sequence was obtained for overlapping clones in both directions for some 2400 bp starting just outside the upstream HindIII site and extending to near the downstream HindIII site. Upstream and downstream are relative to the deduced open reading frame. The nucleotide sequence and deduced amino acid sequence of the protein are shown in FIGS. 16A and 16B.

The active region contains an open reading frame extending from position 188 to position 1668 bp if one allows for a short intron (position 312-388). S1 analysis using a single stranded probe synthesized from an oligonucleotide primer situated at position 795 to 812 (oligonucleotide sequence 5'ggaaccgccattccatc-3') and extending to either the upstream HindIII site (position 1) or an NcoI (position 462) site located the 3'-splice junction of the intron near position 390. The existence of the intron was confirmed by direct messenger RNA sequencing as follows. RNA was prepared from sod2-1 and passed over an oligo U Sepharose column (Pharmacia) to prepare a fraction enriched in polyadenylated messenger RNA. This RNA was used as template for reverse transcriptase primed by an oligonucleotide primer, 5'-tttagcagcatgaggccc-3' (position 415-436). The sequencing reaction was based on the reverse transcriptase DNA sequencing kit from Promega. The sequence confirmed the position of the intron as shown in FIG. 9 and FIGS. 16A and 16B. Downstream of the gene, deletion from position 2063 is active; a deletion from 1600 has a small amount of activity and deletion from 1436 is inactive. Upstream deletion to position 179 is active; deletion to 207 is not.

Relationship of plasmid to sod2-1 mutant strain

The 2.3 kb HindIII fragment in pWH5 was transformed into leu1-32 yeast and an integrant selected by culture on yeast extract media and then on EMM. Similarly the 5'- 3.5 kb EcoRI-HindIII fragment from psod2 was integrated. Each strain was crossed to sod2-1 and the segregation of the leu1-32 marked plasmid integrant and the lithium resistance analyzed. For the 2.3 kb HindIII fragment reassortment of the lithium resistance to all progeny made the analysis meaningless. This was presumed to be due to unequal crossing over with the amplified (see below) sod2 locus in the sod2-1 strain. For the 3.5 kb EcoRI-HindIII integrant the leu1-32 marker integrated at the same site as the 2-3 Kb fragment. Based on these data and the Southern blotting results described below, but recognizing that the amplified nature of the locus in sod2-1 results in unusual recombination frequencies, it is believed that the psod2 plasmid represents the sod2 locus.

Figure 10A:
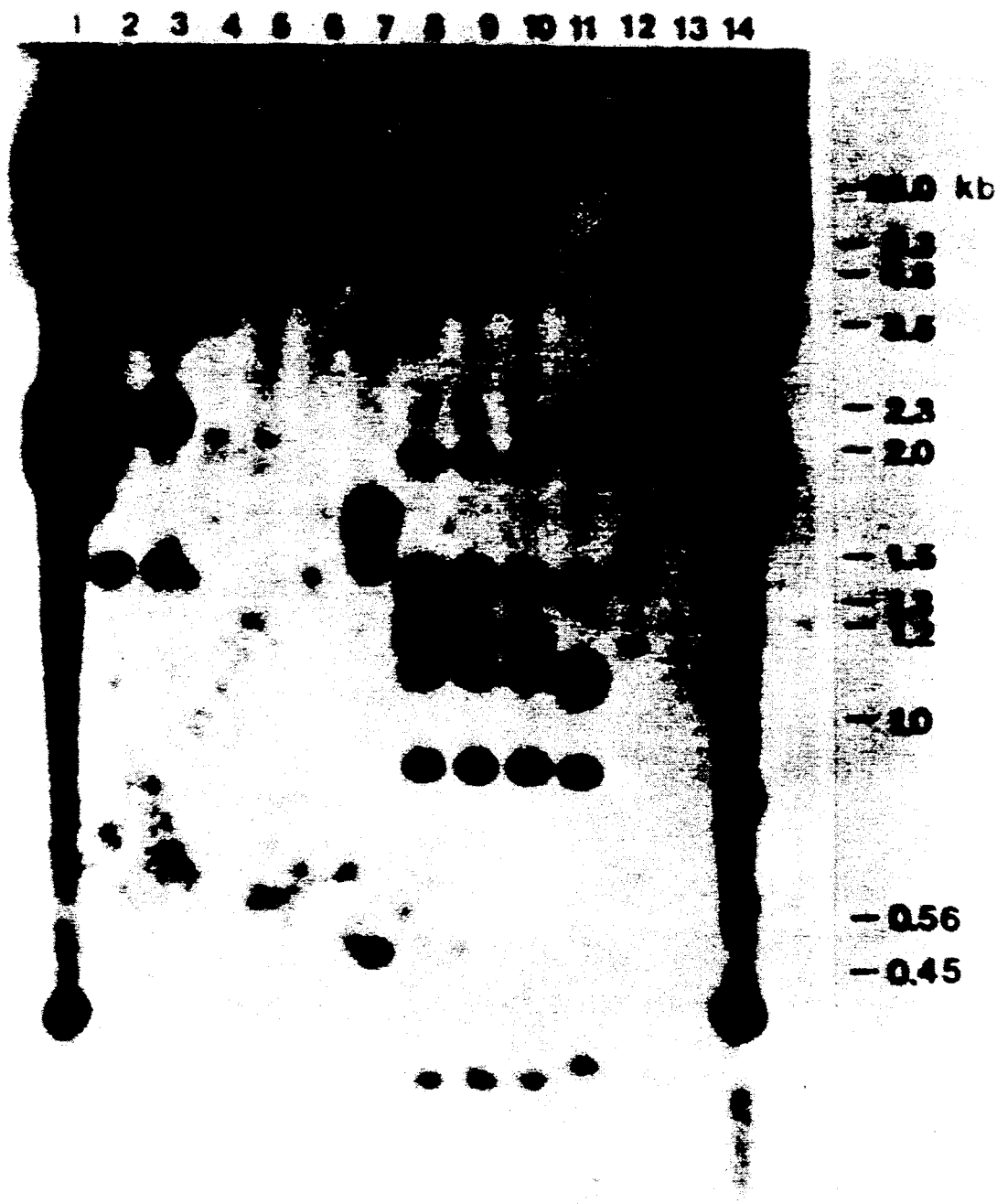
FIG. 10A is a Southern blot analysis of the sod2 gene in wild type *S. pombe* cells using the 5.8 kb genomic insert of psod2 as probe.
Figure 10B:
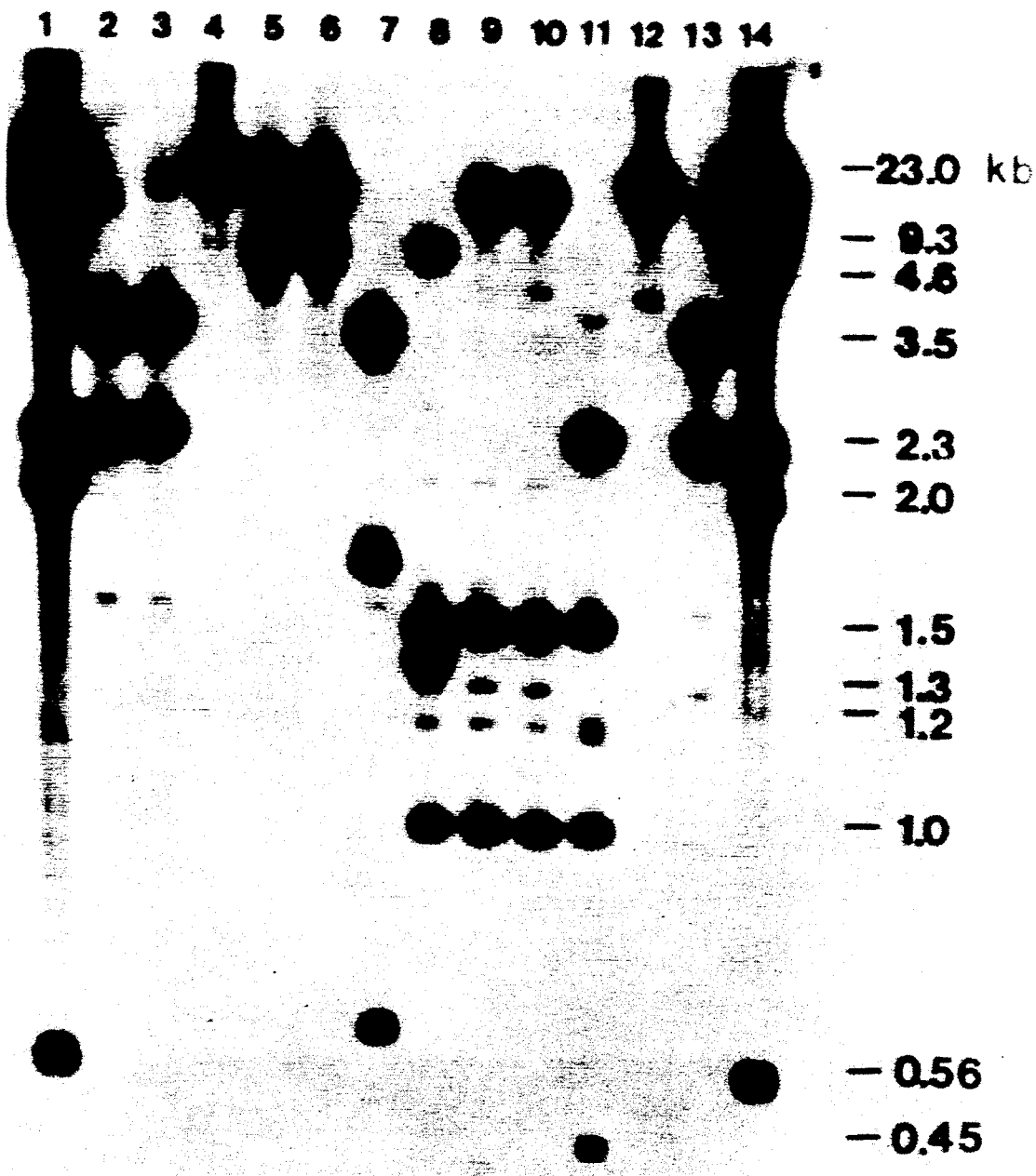
FIG. 10B is a Southern blot analysis of the sod2 gene in sod2-1 cells probed as in 11A.

Southern blotting was used to examine the organization of the gene represented by the psod2 plasmid. Typically DNA was prepared from both wild type and sod2-1 cells, digested with a variety of restriction endonuclease enzymes, electrophoresed and transferred to GeneScreen membranes (New England Nuclear) by Southern blotting. A blot of wild type DNA and of sod2-1 DNA was hybridized (hybridization: 3× SSC (1× SCC =0.15M sodium chloride, 0.015M sodium citrate, pH 7.4) 65° C. overnight; final wash 0.1× SSC, 65° C.) with the nick translated 5.8 kb genomic insert from psod2. Restriction fragments hybridizing to the radioactive probe were identical in wild type DNA and in sod2-1 DNA (FIGS. 10A & B respectively). Lanes 1 and 14, HindIII digested lamda DNA. Remainder of lanes yeast genomic DNA: lane2, HindIII; lane3, HindIII/PstI; lane4, PstI; lane5, PstI/PvuII; lane6, PvuII; lane7, PvuII/HindIII; lane8, PvuII/EcoRI; lane9, EcoRI; lane 10, EcoRI.PstI; lane 11, EcoRI/HindIII; lane 12, A. BamHI/HindIII B. BamHI; lane13, A. BamHI B. BamHI/HindIII. In sod2-1 DNA, however, some of the bands were highly amplified relative to others. Upon equivalent autoradiographic exposure of the blots, band intensity of the weaker signals in the sod2-1 DNA were the same as for wild type DNA. In addition, all similar sized bands in the wild type DNA were of similar intensity. It is, therefore, deduced that the intensity profile of the weaker signals is indicative of single copy genomic DNA fragments. In the HindIII digest of wild type DNA (FIG. 10A) five bands are visible: the 3.1 kb, 2.3 kb and 0.5 kb fragments identified in the psod2 plasmid as well as bands at 1 kb and 5 kb which are not present in plasmid digests. These same bands are present in the sod2-1 DNA however the 3.1 kb, 2.3 kb and 0.5 kb are highly amplified. The entire region represented by the psod 2 clone appears to be amplified. There are additional non-amplified bands however and these appear to represent a second copy of some portion of the psod2 sequence.

Figure 10C:
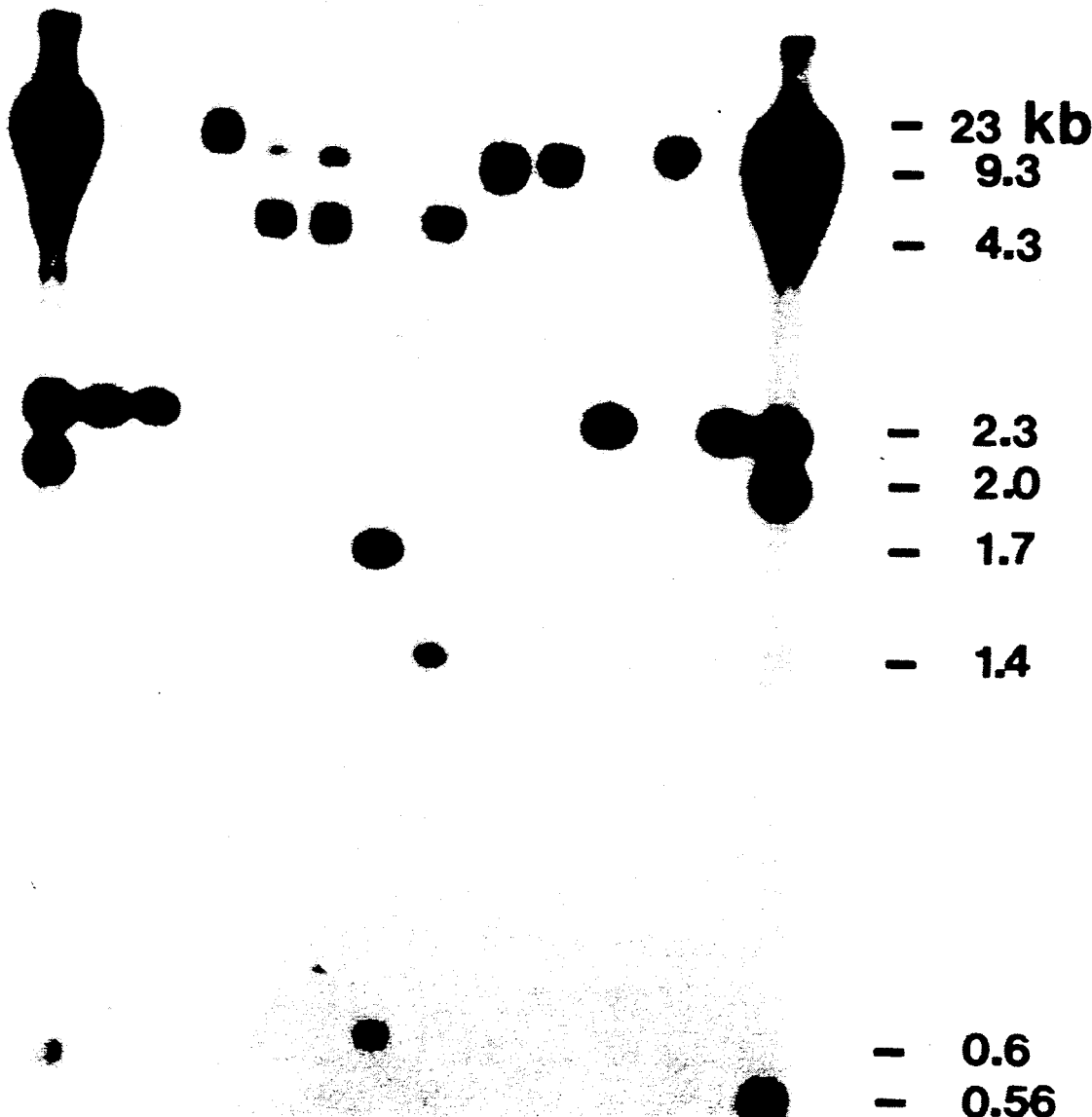
FIG. 10C is a Southern blot analysis of the sod2 gene in sod2-1 cells using the 2.3 kb HindIII genomic insert of psod2 as probe.

When the same blots were hybridized with the psod2 2.3 kb HindIII sequence the additional non-amplified bands were not present. It is concluded that there is only one copy of the psod2 2.3 kb HindIII fragment in the *S. pombe* genome (FIG. 10C).

Intact wild type and sod2-1 DNA was electrophoresed, Southern blotted and probed with the HindIII 2.3 kb fragment. No trace of a rapidly migrating episomic or plasmid band could be detected. It is concluded that the amplification of the sod2 sequence is chromosomally located or present on very large episomic fragments.

A gene bank was prepared in plasmid vector pWH5 using genomic DNA from sod2-1. Using an oligonucleotide probe prepared from the HindIII 2.3 kb fragment of psod2 the equivalent region has been isolated from the mutant. identity was confirmed by sequencing. The sequence was found to be the same/different as the psod2 2.3 kb HindIII fragment. The gene bank was also used to transform wild type cells to lithium/sodium resistance at high frequency consistent with the amplified nature of the sod2 locus in sod2-1.

Construction of a null or inactivated sod2 mutation

The HindIII 2.3 kb fragment of psod2 was subcloned into pUC118 and transformed into dam− JM103 *E. coli*. The plasmid was isolated and digested with restriction endoclease BclI to remove a fragment extending from position 1155 within the open reading frame to position 1955 downstream of the open reading frame. Approximately one half of the open reading frame was thus deleted. The ura4 gene from *S. pombe* was isolated as a HindIII fragment from plasmid pura4. HindIII/BamHI oligonucleotide linkers were ligated to the isolated ura4 gene and the ura4 gene then ligated into the BclI sites of the HindIII 2.3 kb fragment in pUC118. Following preparation the resulting plasmid was transformed into an *S. pombe* diploid strain of genetic constitution ura4-D18/ura4-D18 leul-32/leul-32 ade6-210/ade6-216 and plated onto EMM plus 1.2M sorbitol plus 100 g/mL leucine plates. Following selection for integration 120 strains displaying prototrophy for uracil were characterized for sodium and lithium tolerance. Seven strains were isolated which grew poorly on EMM and could not grow on EMM plus 150 mM NaCl. These strains were presumed to represent gene replacements resulting from double homologous recombination events or insertions at sod2 which hindered the function of the sod2 gene. These strains germinated poorly from the spore on EMM (plus leucine) however grew better on EMM (plus leucine) made by eliminating $Na_2HPO_4$ and replacing it with $K_2HPO_4$ and adjusting the pH to 5.5. Such a formultion has a final sodium concentration of approximately 0.5 mM as compared to EMM with 26 mM Na+ The gene knockout strain sod2::ura4-D18 ura4-D18/ura4-D18 leul-32/leul-32 ade6-210/ade6-216 was used to prepare DNA for a genomic Southern blot to verify the gene elimination. Genomic DNA from several stains was prepared and digested with various restriction enzymes and a Southern blot prepared on GeneScreen following agarose gel electrophoresis. The membranes were then hybridized to the nick translated 2.3 kb genomic fragment from psod2 at high stringency. The result showed that the HindIII 2.3 kb fragment is missing from the sod2::ura4 strain (FIG. 11). Lanes 1–5, BclI digested; lanes 6–10, HindIII digested. Lanes 1, 6 osd2-1: lanes 2, 7 inactivated strain K35-1; lanes 3, 8 inactivated strain K88-1; lanes 4, 9 inactivated strains K16-2; lanes 5, 10 inactivated strain K15-5. This fragment was thus disrupted. K15-5 was used for further experiments.

The phenotype of the disruptant was sodium sensitivity, lithium sensitivity and ammonium sensitivity. The latter presumably results from cytoplasmic alkalinization by ammonia and the sod2 gene, as a putative proton antiport, in part plays a role in pH regulation.

Construction of an Overexpression Plasmid

Figure 12:
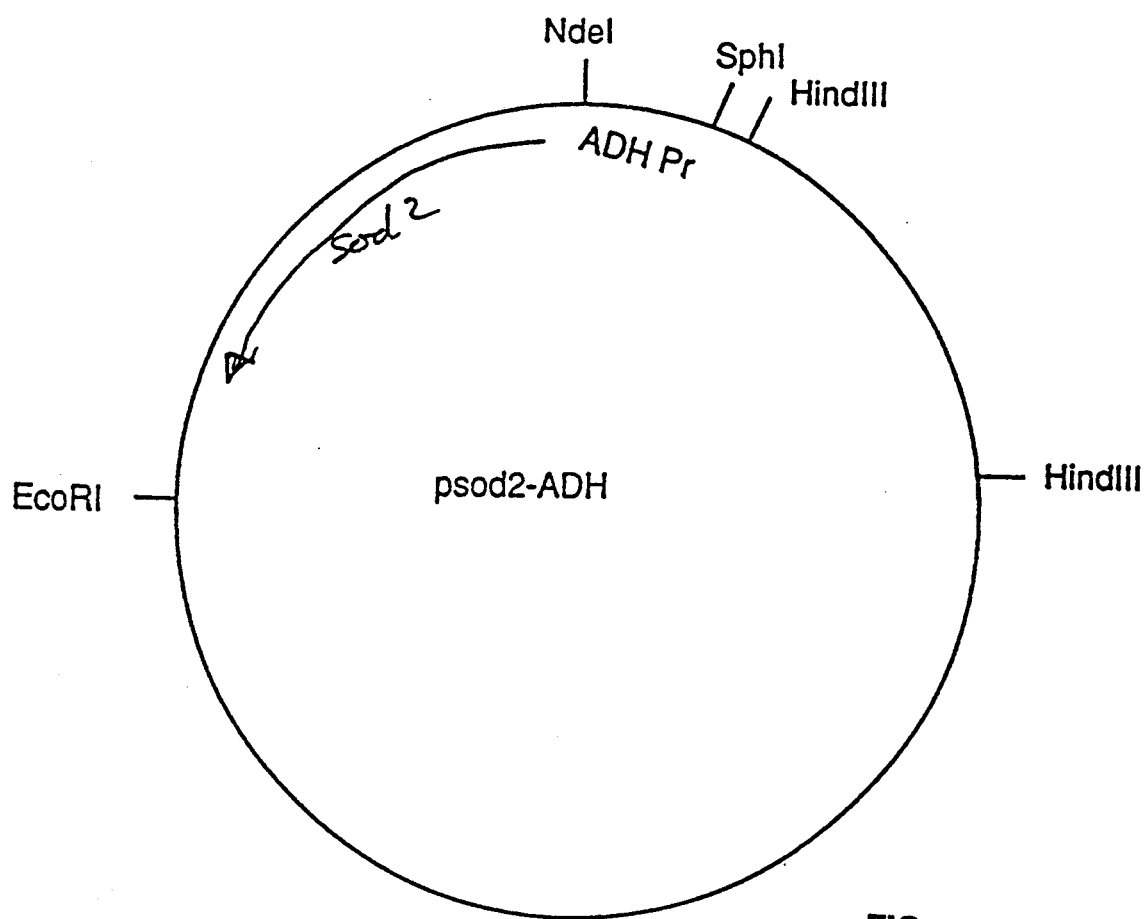
FIG. 12 is a plasmid map of psod2-ADH1.
Figure 13:
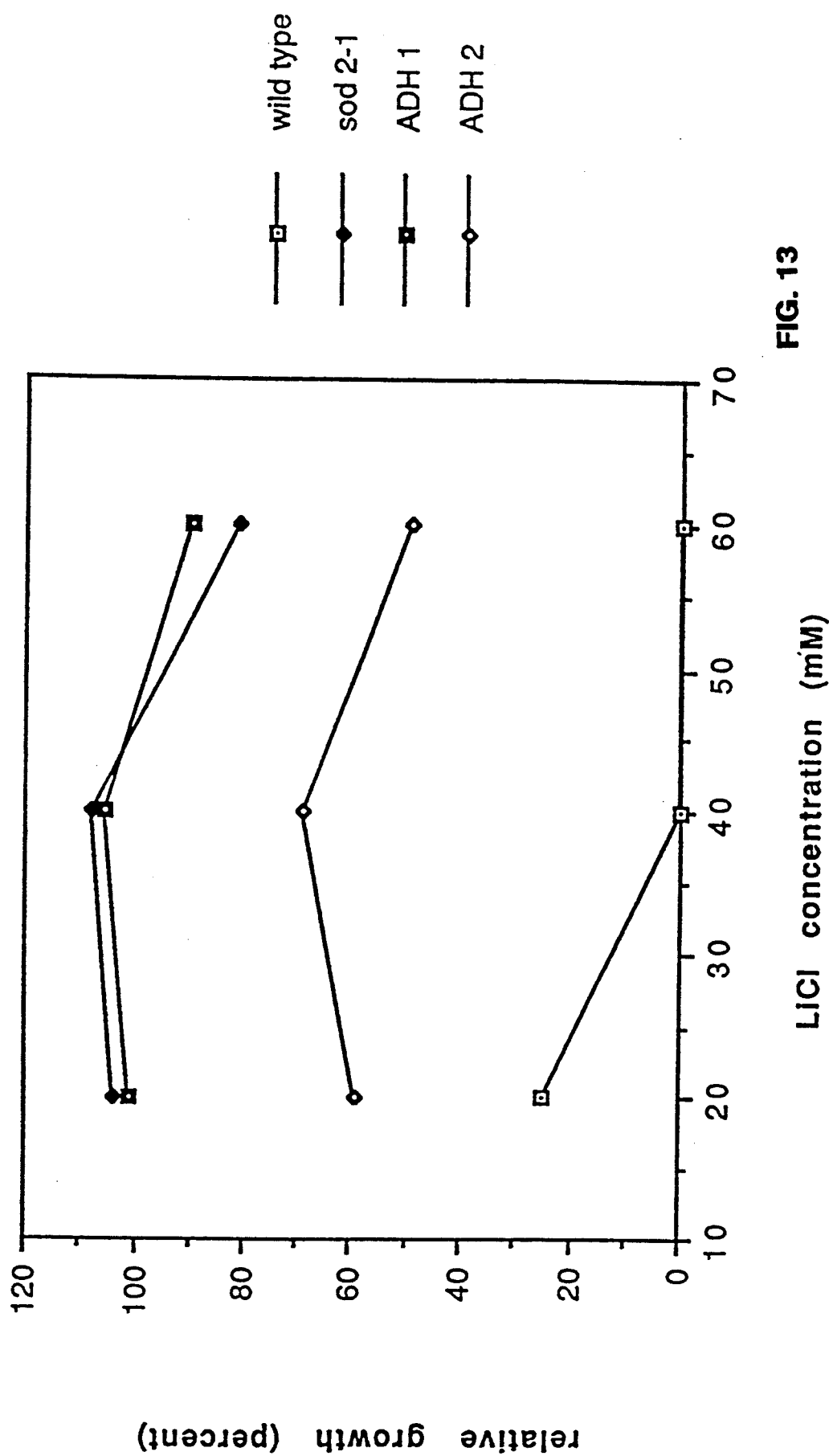
FIG. 13 is a graph showing growth of wild type, sod2-1, psod2-ADH1 and psod2-ADH2 strains on agar plates containing LiCl.

Since gene amplification plays a role in sod2-1 mutant function, construction of a plasmid containing a strong promoter linked to the open reading frame from psod2 should function to cause sodium tolerance after reintegration into the genome. The plasmid pART5 containing the alcohol dehydrogenase promoter was used. An NdeI site was inserted by oligomutagenesis at the putative start codon of the sod2 open reading frame at position 188 (using a mutagenic oligonucleotide 5'-ttgcctaattcatatgggctgg-3'). Subsequent to the removal of an internal NdeI site at position 630 (using a mutagenic oligonucleotide 5'-ctggatttgcgtatgcattgt-3') the gene was excised from pUC119 as an NdeI-EcoRI fragment and ligated into pART5 to generate plasmid psod2-ADH (FIG. 12). Following construction the plasmid psod2-ADH was transfected into a leul-32ura4-D18ade6-210 *Schizosaccharomyces pombe* strain and plasmid integrated strains selected by growth on YEA medium and selection on EMM supplemented with uracil and adenine. The plasmid containing strains were then tested for LiCl and NaCl tolerance. Wild type, sod2-1 and psod2-ADH int leul-32 strains were plated onto EMM agar plates containing LiCl at the concentrations indicated. (FIG. 13: ADH1=psod2-ADH1 and ADH2=psod2-ADH2). Growth was determined as for FIG. 1 and expressed relative to ADH1 on 20 mM LiCl as 100 percent. A strain overexpressing the sod2 gene behind an ADH promoter is strongly Li+ and Na+ tolerant Differences in resistance among the different ADH strains presumably reflects the particular context of genomic integration in each case. Similar constructions based on inserting NdeI restriction sites at the in frame ATG at positions 670 or 830 were inactive with respect to lithium tolerance upon subsequent transformation into yeast.

A version of psod2-ADH from which the interon, as defined in FIGS. 16A and 16B, had been removed by obigomutogenesis is also functional and confers the same level of sodium/lithium tolerance as the intron plus version of the gene.

Sodium efflux from sod2-1 and psod2-ADH1 strains

Figure 14:
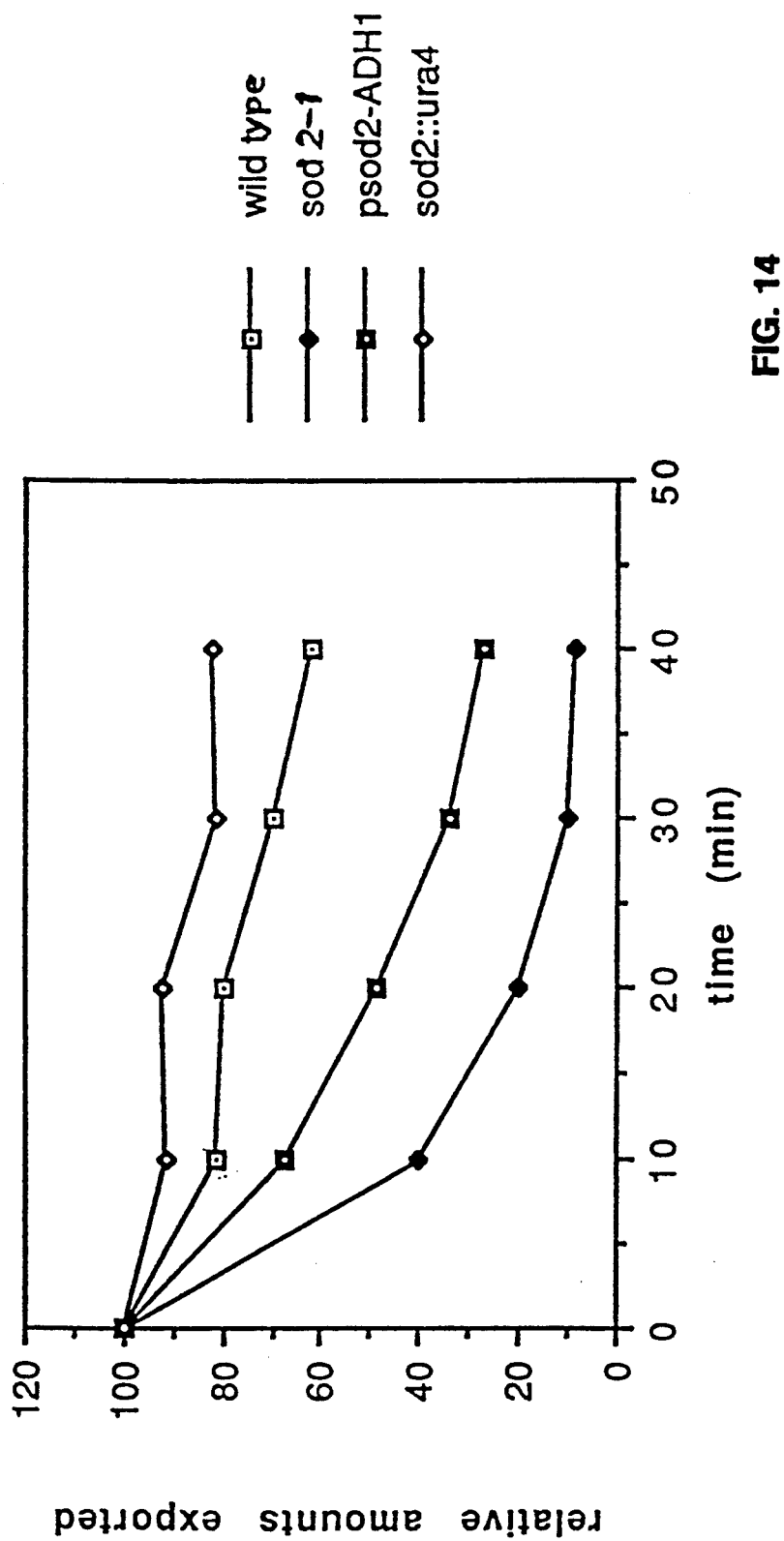
FIG. 14 is a graph illustrating sodium export in the absence of external sodium for wild type, sod2-1, psod2-ADH1 Leu1-32 and sod2::ura4.

Wild type, sod2-1, psod2-ADH1 and sod2::ura4 strains were labelled with $^{22}Na$ as described above and the export of Na from the cell monitored following resuspension in MES/PIPES buffer with 6 mM NaCl or in sodium free MES/PIPES buffer. The sod2-1 and the psod2-ADH1 strains exported sodium more rapidly than wild type under both conditions. The sod2::ura4 strain exported more slowly than wild type (FIGS. 14, 15).

Heterologous DNA with sequence similarity to sod2

A southern blot analysis of other species of yeast including Schizosaccharomyses (japoricus and octosporus) and *Saccharomyces cerevisiol*. No hybridization signal was found for *S. cerevisial*. In the case of both *Schizosaccharomyces octosporus* a hybridization signal was found. It is concluded that these two yeasts may harbour a gene similar to sod2 from *S. pombe*.

I claim:

1. A sodium tolerant strain of *S. pombe*, sod2-1, ATCC 74028.

2. An isolated gene having the sod 2 nucleotide sequence shown in FIG. 16A and B.

* * * * *